United States Patent [19]

Walker et al.

[11] Patent Number: 4,927,963
[45] Date of Patent: May 22, 1990

[54] NOVEL PROCESSES FOR THE SYNTHESIS OF CERTAIN BICYCLO(4.2.0)OCTANE DERIVATIVES WITH VALUABLE THERAPEUTIC PROPERTIES

[75] Inventors: Keith A. M. Walker, Los Altos Hills; Denis J. Kertesz, Mountain View, both of Calif.

[73] Assignee: Syntex (U.S.A.) Inc., Palo Alto, Calif.

[21] Appl. No.: 346,425

[22] Filed: Apr. 28, 1989

[51] Int. Cl.$^5$ .............................................. C07C 62/32
[52] U.S. Cl. .................... 562/501; 549/336; 549/337; 562/466; 562/462; 562/499; 568/347; 568/374
[58] Field of Search ......................................... 562/501

[56] References Cited

U.S. PATENT DOCUMENTS

| | | | |
|---|---|---|---|
| 4,238,414 | 12/1980 | Morton | 564/453 |
| 4,306,076 | 12/1981 | Nelson | 560/56 |
| 4,487,960 | 12/1984 | Lin | 560/256 |
| 4,487,961 | 12/1984 | Aristoff | 562/501 |
| 4,680,388 | 8/1986 | Kluge | 514/510 |
| 4,735,966 | 4/1988 | Wu | 562/501 |

FOREIGN PATENT DOCUMENTS 1215362 12/1986 Canada .

*Primary Examiner*—Michael L. Shippen
*Attorney, Agent, or Firm*—Brian Lewis; Tom Moran

[57] ABSTRACT

A process for preparing compounds represented by the formula

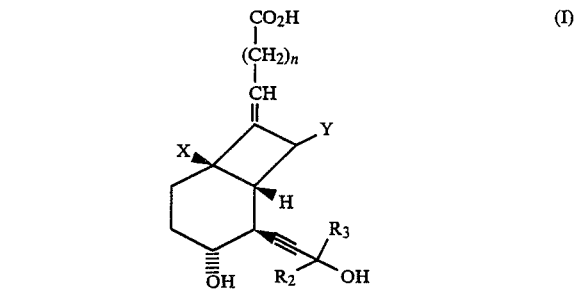

wherein:
X is hydrogen or lower alkoxy;
Y is hydrogen, exo-(lower alkyl) or endo-(lower alkyl);
n is an integer from 2–4;
R$_2$ is hydrogen or methyl; and
R$_3$ is linear or branched alkyl,

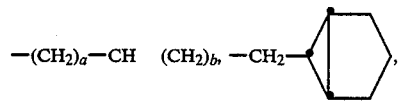

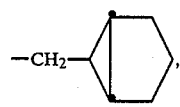

—(CH$_2$)$_m$-phenyl or —CH$_2$O-phenyl;
in which any phenyl may be optionally substituted with lower alkyl, lower alkoxy, trifluoromethyl, or halogen, and
a is an integer of 0, 1 or 2;
b is an integer of 3–7;
m is an integer of 0, 1 or 2,
as a mixture or separately in a sequence starting from an epoxide represented by the formula

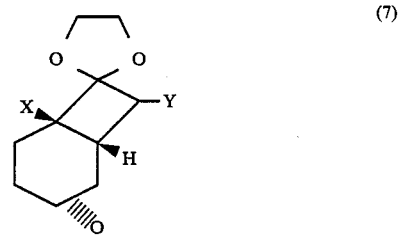

and processes for making the novel intermediates.

11 Claims, No Drawings

PROCESSES FOR THE SYNTHESIS OF CERTAIN BICYCLO(4.2.0)OCTANE DERIVATIVES WITH VALUABLE THERAPEUTIC PROPERTIES

This is a division of pending application Ser. No. 064,156, filed Jun. 19, 1987.

BACKGROUND OF THE INVENTION

1. Field of the Invention

This invention relates to a novel process for the synthesis of certain bicyclo[4.2.0]octane derivatives, useful for treating cardiovascular disorders.

2. Related Disclosures

Methods for the synthesis of certain bicyclo[4.2.0]octane derivatives, useful for treating cardiovascular disorders, were disclosed in U.S. Pat. No. 4,608,388, U.S. patent application Ser. No. 891,509 and U.S. patent application Ser. No. 900,025, the relevant portions of which are hereby incorporated by reference.

Several prostaglandin analogs are known which contain bicyclic all-carbon skeletons, and the processes by which they are made are described in several publications and patents (U.S. Pat. No. 4,238,414; U.S. Pat. No. 4,306,076; Ger. Offen. No. 3,146,278; Ger. Offen. No. 3,204,443; *Prostaglandins, Leukotrienes. Med.* 11:391, 1983). 9-Substituted analogs of carbacyclin are described in U.S. Pat. No. 4,487,960 and U.S. Pat. No. 4,487,961.

SUMMARY OF THE INVENTION

In a first aspect the present invention provides a novel process for the preparation of a single stereoisomer, or a mixture of stereoisomers, of a compound represented by the formula (I):

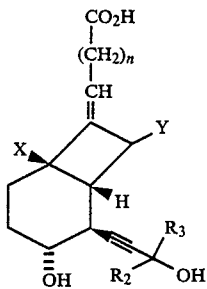

wherein:
X is hydrogen or lower alkoxy;
Y is hydrogen, exo-(lower alkyl) or endo-(lower alkyl);
n is an integer of 2-4;
$R_2$ is hydrogen or methyl; and
$R_3$ is linear or branched alkyl,

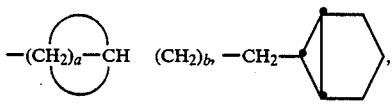

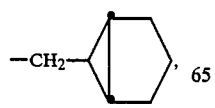

—$(CH_2)_m$-phenyl or —$CH_2O$-phenyl;

in which any phenyl may be optionally substituted with lower alkyl, lower alkoxy, trifluoromethyl, or halogen, and a is an integer of 0, 1 or 2;
b is an integer of 3–7;
m is an integer of 0, 1 or 2, which process comprises starting from a single stereoisomer, or a mixture of stereoisomers, represented by the formula (7):

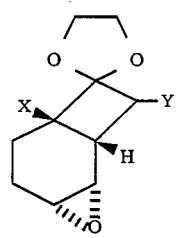

(7)

and includes the following reaction steps:

REACTION SCHEME I

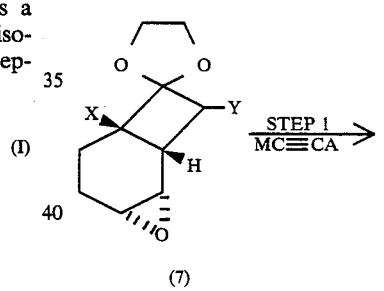

(7)

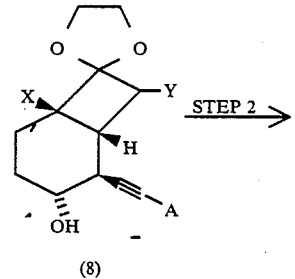

(8)

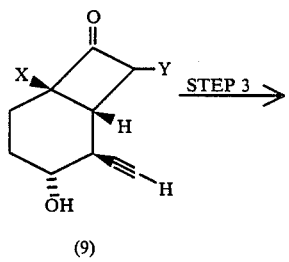

(9)

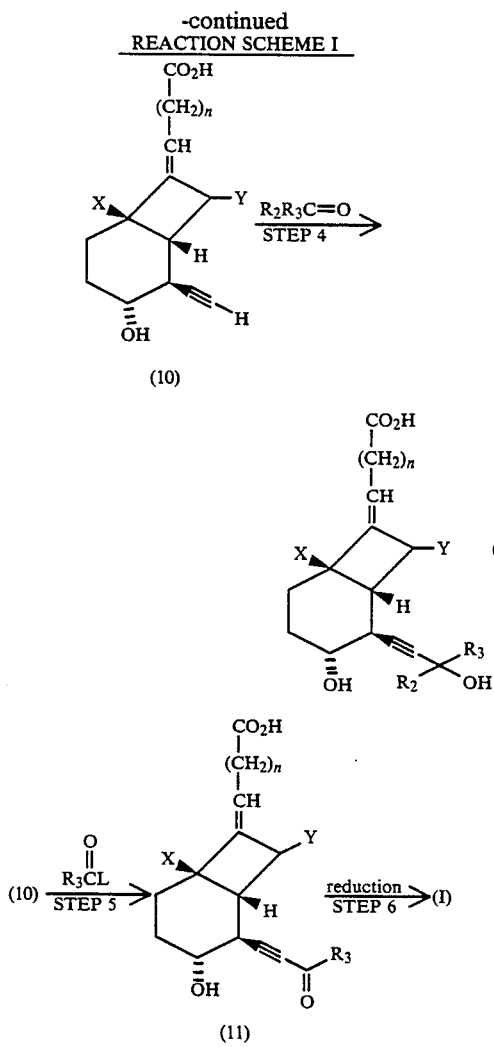

where L is a leaving group.

Further aspects of the invention comprise each of the individual steps of Reaction Scheme IA and IB, i.e. steps 1–6.

In still further aspects, the invention relates to novel compounds of the formula (8), (9), (10) and (11) which are useful as intermediates in the processes described and claimed herein.

DETAILED DESCRIPTION OF THE INVENTION

Definitions

The term "alkyl" refers to and includes saturated branched and straight chain monovalent hydrocarbon radicals. Typical alkyl groups include methyl, ethyl, propyl, isopropyl, butyl, tertiary butyl, neopentyl, isopentyl, hexyl, octyl, nonyl, isodecyl, 6-methyldecyl.

"Cycloalkyl" as used herein means a saturated monovalent monocyclic hydrocarbon radical containing 3–8 carbon atoms, such as cyclopropyl, cyclobutyl, cyclopentyl, cyclohexyl, cycloheptyl and cyclooctyl.

The term, "lower alkyl" refers to a branched or unbranched saturated monovalent hydrocarbon chain of 1–4 carbons, such as, for example, methyl, ethyl, n-propyl, i-butyl and the like.

The term, "lower alkylthio" refers to a branched or unbranched saturated monovalent hydrocarbon chain of 1–4 carbons attached to a sulfur atom, such as, for example, methylthio, ethylthio, n-propylthio, i-butylthio and the like.

The term "alkoxy" refers to the radical -O-alkyl wherein "alkyl" is as defined above. This includes radicals such as methoxy, ethoxy, 2-propoxy, butoxy, 3-pentoxy and the like.

"Lower alkoxy" means the group -O-(lower alkyl) wherein lower alkyl is as defined above.

"Halo" as used herein denotes fluoro, chloro, bromo, or iodo.

"Phenyl" as used herein encompasses all possible isomeric phenyl radicals optionally monosubstituted with a substituent selected from the group consisting of lower alkyl, lower alkoxy, hydroxy, trifluoromethyl and halogen.

"BINAL-H" is an abbreviation for binaphthol-modified complex aluminum hydride, a chiral reducing agent, prepared in situ by mixing lithium aluminum hydride, a hydroxylic compound, preferably methanol or ethanol, and either (S) or (R) 2,2'-dihydroxy-1,1'-binaphthyl, in a 1:1:1 mole ratio.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

The terms "$\alpha$ and $\beta$" indicate the specific stereochemical configuration of a substituent at an asymmetric carbon atom in a chemical structure as drawn. Thus "$\alpha$", denoted by a broken line, indicates that the group at the position in question is below the general plane of the molecule as drawn, and "$\beta$", denoted by a bold line, indicates that the group at the position in question is above the general plane of the molecule as drawn.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror-images of each other.

"Epimers" are diastereoisomers which differ only in the configuration of one asymmetric center.

"Racemic mixture" means a mixture containing equal parts of individual enantiomers. "Non-racemic mixture" is a mixture containing unequal parts of individual enantiomers.

The term "ylide or stabilized anion normally associated with an olefination reaction" refers to compounds of the type $(R')_3P=CR''R''$ (ylides), or $(R'O)_2P(O)\bar{C}R''R''$ or $(R')_2P(O)\bar{C}R''R''$ (stabilized anions), where R' is alkyl or phenyl and R" is independently hydrogen or alkyl optionally substituted with, for example, $-(CH_2)_nCO_2R''$, $-(CH_2)_nCN$ and the like. Such compounds react with an aldehyde or ketone to give an olefin where the position of the double bond is predictable. Ylides and stabilized anions where phosphorus is replaced by sulfur, silicon or nitrogen are also known and are included in this definition.

The numbering system for the bicyclo[4.2.0]octane system shown in the scheme illustration below is used in naming the intermediates and product compounds of the invention.

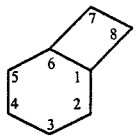

The absolute stereochemistry at carbons 1,2,3 and 6, and 3' of the side chain attached to carbon 2 are specified according to the Cahn-Ingold-Prelog R-S system. When the compound is a pure enantiomer, the stereochemistry at each chiral carbon is specified by either R or S. When a compound is a racemic mixture the stereochemistry at each chiral carbon is specified by either RS or SR by reference to a single enantiomer of the racemate. In this manner relative stereochemistry is conveyed unambiguously. The stereochemistry at carbon 8 is specified as an exo or endo isomer. When the substituent Y at carbon 8 is cis to the ring junction substituents H and X (at carbons 1 and 6) it is specified as an exo-isomer. When the substituent Y at carbon 8 is trans to the ring junction substituents X and H it is specified as an endo-isomer. Olefin stereochemistry is specified by the IUPAC E - Z system. Classical nomenclature is used to name a compound having a triple bond as alkynyl; and two bonds emanating from the same atom as -ylidene.

The compounds represented by the structure (I) include each of the individual stereoisomers represented below as (Ia), (Ib), (Ic) and (Id), each of which can exist as an E isomer, a Z isomer or a mixture of both. Mixtures of the stereoisomers in any proportion, all as the E isomers or all as the Z isomers, are also represented by the formula (I).

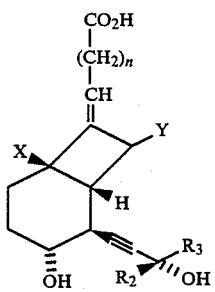

(Ia)

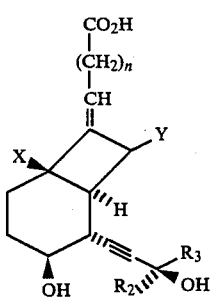

(Ib)

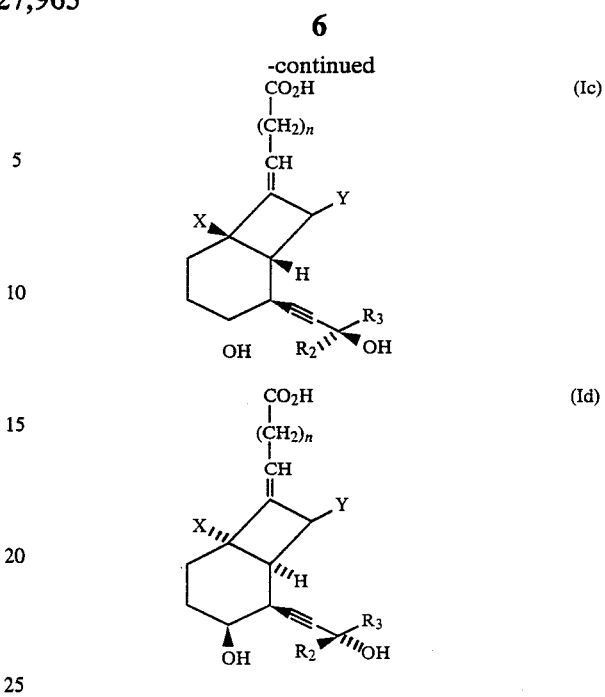

Any individual stereoisomer may be prepared by processes described below, starting from the appropriate individual enantiomer of a compound of formula (7), (8), (9), (10) and (11). Mixtures of (Ia), (Ib), (Ic) and (Id) in any proportion, all as the E isomers or all as the Z isomers, are produced depending on which appropriate racemic or non-racemic modification of the compound of formula (7), (8), (9), (10) and (11) is used as a starting material and which process is chosen to arrive at the compound of formula (I).

For the sake of simplicity, only one stereoisomer will be depicted in the description of the process. However, it is to be understood that the racemic and non-racemic mixtures and all possible individual stereoisomers are also encompassed thereby, they being obtained by starting with the corresponding racemic or non-racemic mixture of the appropriate stereoisomer of formula (7), (8), (9), (10) and (11). For example, the depiction of the compound of formula (7), where Y is hydrogen or exo-(lower alkyl) or endo-(lower alkyl), is intended to represent not only the structure as drawn, but also the opposite enantiomer (mirror image) and all racemic or non-racemic mixtures thereof. In the case where Y is a mixture of exo- and endo-(lower alkyl) (7) represents a mixture of two optically pure enantiomers and their mirror images and all racemic or non-racemic mixtures thereof.

The term "mixture of stereoisomers", as applied to formula (I) is defined in the present application as any combination or permutation of two or more of the individual stereoisomers of formula (Ia), (Ib), (Ic) and (Id) as depicted above, (all as the E isomers or all as the Z isomers), in any proportions.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, or a combination of these procedures. Specific illustrations are described in the Examples. However, other equivalent separation or purification procedures can be used.

The compounds of formula (I) prepared by the present processes are useful for treating cardiovascular diseases, such as atherosclerosis, thrombotic conditions, vasospastic conditions, hypertension and the like.

The present processes are illustrated in more detail in the Reaction Schemes below. The novel processes of the present invention may begin with the compound of formula (7), preferably as a single enantiomer. The preparation of the compound of formula (7), as a single enantiomer or a racemic mixture, is shown in Reaction Scheme II below, starting from a compound of formula (3) as a single enantiomer or a racemic mixture.

The preparation of the compound of formula (3) as a racemic mixture is shown in Reaction Scheme II and described in detail in the subsequent discussion. The individual enantiomers of the compound of formula (3), in which X and Y are hydrogen, are prepared from the racemic compounds of formula (2), in which X and Y are hydrogen, by the method shown in U.S. patent application Ser. No. 900,029, filed Aug. 25, 1986, which is hereby incorporated by reference. The individual enantiomers of the compound of formula (3), in which at least one of X and Y is not hydrogen, are prepared from the corresponding racemic compounds of formula (2A), (2B) or (2C), by the procedures shown in U.S. patent application Ser. No. 900,025, filed Aug. 25, 1986, the relevant portions of which are hereby incorporated by reference.

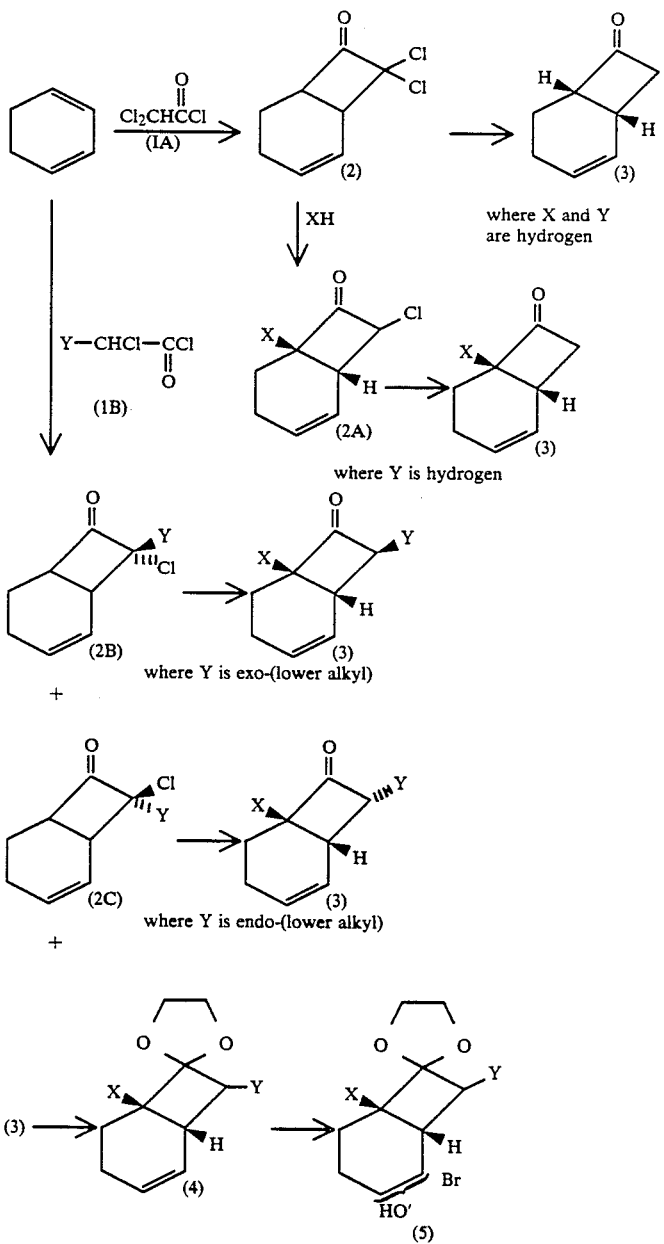

REACTION SCHEME II

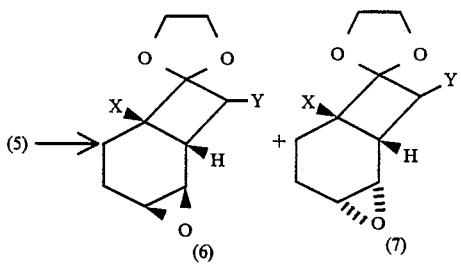

(5) →  (6)  +  (7)

-continued

In the first step, cyclohexadiene and a chloroalkanoyl chloride of formula (1A) or (1B) are reacted together. For example, to prepare the compound of formula (2), cyclohexadiene is reacted with about 0.5 to 1.0 molar equivalents, preferably about 0.75 molar equivalents, of dichloroacetyl chloride, the compound of formula (IA), in an ethereal solvent, such as tetrahydrofuran, 1,2-dimethoxyethane, dioxane or preferably diethyl ether in the presence of about 0.5 to 1.0 molar equivalents, preferably about 0.75 molar equivalents, of triethylamine. The reaction is carried out at a temperature of about 20° C. up to the reflux temperature of the chosen solvent, preferably about 35° C., for about 1 to 6 hours, preferably about 3 hours. The reaction mixture is then stirred at a temperature of about 0°–30° C., preferably about 23° C., for about 8 to 48 hours, preferably about 20 hours. When the reaction is substantially complete, the product of formula (2) is isolated by conventional means.

To prepare the compound of formula (3) where X and Y are hydrogen, the dihaloketone of formula (2) is dehalogenated with a mild dehalogenating agent, for example, tributyltin hydride, a zinc-copper couple or preferably zinc in acetic acid. Typically, the dichloroketone is dissolved in an organic carboxylic acid, preferably acetic acid and reacted with about 2 to 10 molar equivalents, preferably about 5 molar equivalents, of zinc dust at a temperature of about 50°–70° C., preferably about 70° C., for about 20 minutes to 2 hours, preferably about 1 hour. A further quantity of zinc, about 2 molar equivalents, is then optionally added and the mixture heated at about 70°–100° C., preferably about 75° C., for about 20 minutes to 2 hours, preferably about 1 hour. When the reaction is substantially complete the product of formula (3) where X and Y are hydrogen is isolated and purified by conventional means.

Similarly, to prepare the compound of formula (3) where X is hydrogen and Y is exo- or endo-(lower alkyl), the chloroketones of formula (2B) or (2C) are dehalogenated as shown above. It should be noted that dehalogenation of the compound of formula (2B), (where Y is exo), also gives some endo-(lower alkyl) product as an impurity.

To prepare the compound of formula (3) where X is lower alkoxy and Y is hydrogen, the compound of formula (2) is first reacted with the appropriate alcohol of formula XH. For example, the compound of formula (2) is reacted in the presence of 1 to 2 molar equivalents, preferably about 1.1 molar equivalents, of a base such as a sodium lower-alkoxide or a tertiary organic base such as N-methylpiperidine, pyridine or preferably triethylamine with a lower alcohol of formula XH, such as methanol, ethanol and the like, as a solvent. The reaction is carried out at a temperature of about 0°–40° C., preferably about 23° C., for about 1 to 5 hours, preferably about 1½ hours, giving the compound of formula (2A). To the reaction mixture is then added about 1 to 4 molar equivalents, preferably about 3 molar equivalents, of a zinc-copper couple. The reaction is carried out at a temperature of about 0°–40° C., preferably about 23° C., for about 1 to 10 hours, preferably about 3 hours. When the reaction is substantially complete, the compound of formula (3) where X is lower alkoxy and Y is hydrogen, is isolated by conventional means.

Similarly, to prepare the compound of formula (3) where X is lower alkoxy and Y is lower alkyl, cyclohexadiene is first reacted with the appropriate 2-chloroalkanoyl chloride of formula (1B) in the same manner as discussed above for the preparation of the compound of formula (2). The mixture of exo-(lower alkyl) compound (2B) and endo-(lower alkyl) compound (2C) thus produced is then separated into the individual isomers (2B) and (2C) by conventional means, preferably chromatography. For example, to prepare the compounds of formula (2B) and (2C) where Y is methyl, cyclohexadiene is reacted with 2-chloropropionyl chloride.

The compound of formula (2B) or (2C) is then reacted with the appropriate alcohol of formula XH in the same manner as discussed above for the preparation of the compound of formula (2A), giving the compound of formula (3) where X is lower alkoxy and Y is exo-(lower alkyl) or endo-(lower alkyl), which is isolated conventionally.

The subsequent preparative procedures of Reaction Scheme II will be described without specifying the stereochemistry of the 8-(lower alkyl) group, where present. However, it should be understood that the preparations described are applicable equally to the 8-exo-(lower alkyl) or the 8-endo-(lower alkyl) compounds, unless indicated otherwise, and that both isomers are intended to fall within the scope of these preparations.

The compound of formula (3) is then reacted with about 1 to 10 molar equivalents, preferably about 5 molar equivalents, of ethylene glycol in a solvent such as toluene, xylene or preferably benzene in the presence of an acid catalyst such as hydrochloric acid, methanesulfonic acid or preferably p-toluenesulfonic acid. The reaction is carried out at the reflux temperature of the solvent used, removing water azeotropically, typically for about 1 to 10 hours, preferably about 4 hours. When the reaction is substantially complete, the product of formula (4) is isolated and purified by conventional means.

The compound of formula (4) is then reacted with about 1 to 2 molar equivalents, preferably about 1.2 molar equivalents, of a halogenating agent such as N-chlorosuccinimide or preferably N-bromoacetamide in an aqueous solvent mixture such as acetone-water. This is the preferred procedure for the preparation of compounds of formula (5) where Y is lower alkyl. The reaction is initially carried out at about 0° C. for about 1 hour, then at a temperature of about 5°–40° C., preferably about 25° C., for about 8 to 40 hours, preferably about 20 hours. To this solution is added about 2 to 5 molar equivalents, preferably about 3 molar equivalents, of a base such as sodium hydroxide, sodium bicarbonate or preferably potassium carbonate, and the mixture stirred at a temperature of about 0°–40° C., preferably about 25° C., for about 12 hours to 3 days, preferably about 1 day. When the reaction is substantially complete, the mixture of compounds of formula (6) and (7) is isolated and purified by conventional means.

Alternatively, the compound of formula (4) is reacted with about 1 to 2 molar equivalents, preferably about 1.1 molar equivalents, of an epoxidizing agent such as peracetic acid, perbenzoic acid or preferably m-chloroperbenzoic acid. This is the preferred procedure for the preparation of compounds of formula (7) where Y is hydrogen (which also produces the unwanted epoxide of formula (6)). The reaction is carried out in an inert solvent such as chloroform, cyclohexane or preferably methylene chloride, at a temperature of about 0°–40° C., preferably about 25° C., for about 1 to 10 hours, preferably about 3 hours. When the reaction is substantially complete, the mixture of compounds of formula (6) and (7) is isolated and purified by conventional means.

The preferred process for the preparation of the compounds of formula (I) starts from a single enantiomer of the compound of formula (7), which is obtained from the corresponding single enantiomer of the compound of formula (3), by the reaction sequence shown in Reaction Scheme II above, giving a mixture of optically pure (7) along with the unwanted compound of formula (6).

The novel processes of the present invention include the preparation of compounds of formula (I) from the compounds of formula (7), (8), (9) and (10), successively by the reactions designated as Steps 1–4, as illustrated in Reaction Scheme IA below.

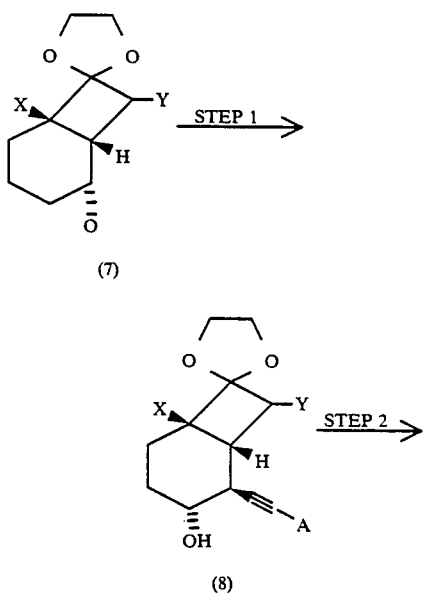

(7)

(8)

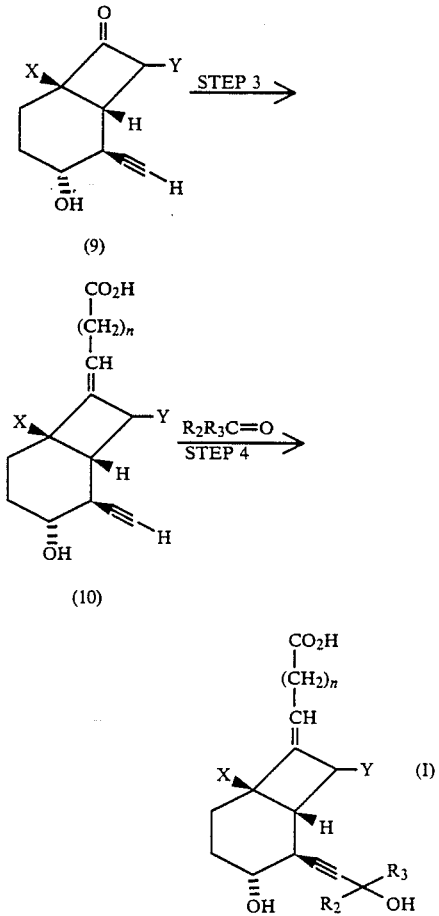

(9)

(10)

(I)

The reaction of Step 1, in its broadest aspect, comprises reacting a compound of formula (7) with a compound of the formula MC≡CA, in which M is an alkali metal and A is hydrogen or a protecting group, to give a compound of formula (8). In actual practice, a mixture of bicyclic epoxyketals (6) and (7), preferably as single enantiomers, obtained in the synthesis of the compound of formula (7) as described above in Reaction Scheme II, is reacted with a compound of the formula MC≡CA, where M is for example sodium, potassium or preferably lithium, and A is a protecting group, for example trimethylsilyl or preferably hydrogen, in the presence of boron trifluoride etherate to give the compound of formula (8). In the reaction of the metal acetylenic reagent with the mixture of epoxyketals (6) and (7), both α and β epoxides undergo reaction, and the attack by the lithium acetylide reagent is not regioselective. Thus the reaction gives a mixture from which the desired compound of formula (8) is separated by chromatography. To carry out this process, the epoxides are reacted with about 1 to 5 molar equivalents, preferably about 2 molar equivalents, of the metal acetylide of formula MC≡CA, where M is preferably lithium and A is preferably hydrogen, (prepared by reacting acetylene of formula HC≡CH with about one molar equivalent of butyllithium), in the presence of about 1 to 4 molar equivalents, preferably about 2 molar equivalents, of boron trifluoride etherate. The reaction is carried out in an ethereal solvent, as defined above, preferably tetrahydrofuran, for about 30 minutes to 4 hours, preferably 1 hour, at a temperature of about −20° C. to −100° C., preferably about −78° C. When the reaction is substantially complete, the compound of formula (8) is isolated and purified by conventional means.

The reaction of Step 2, in its broadest aspect, comprises reacting a compound of formula (8) with an acid to give the ketone of formula (9). The compound of formula (8), preferably as a single enantiomer, is dissolved in an inert solvent miscible with water, for example methanol, acetone, or preferably acetonitrile, and stirred with about 1 to 10 molar equivalents, preferably about 5 molar equivalents, of an acid catalyst, such as hydrochloric acid, p-toluenesulfonic acid or preferably sulfuric acid in water. The reaction is carried out at a temperature of about 0°–80° C., preferably about 50° C., for 2–48 hours, preferably about 16 hours. When the reaction is substantially complete, the ketone of formula (9) is isolated and purified by conventional means.

The reaction of Step 3, in its broadest aspect, comprises reacting a compound of formula (9) with an ylide or stabilized anion normally associated with an olefination reaction to give a compound of formula (10). For example, a phosphorus ylide of formula $(R')_3P=CH(CH_2)_nCOOH$, where $R'$ is optionally substituted phenyl, prepared from the corresponding phosphonium salt, or a stabilized anion prepared from a compound of the formula $(R'O)_2P(O)CH_2(CH_2)_nCO_2H$ where $R'$ is alkyl or optionally substituted phenyl, or $(R')_2P(O)CH_2(CH_2)_nCO_2H$ where $R'$ is optionally substituted phenyl.

Preferably, triphenylphosphine is reacted with an appropriate ω-halocarboxylic acid as described in *J. Org. Chem.*, 27, 3404 (1962). The resulting phosphonium salt is slurried in an aprotic solvent such as diethyl ether, tetrahydrofuran or preferably dimethyl sulfoxide, at a temperature of about 0°–40° C., preferably about 25° C., and about 2.2 molar equivalents of a strong base added, such as butyl lithium, sodium amide, potassium hydride, sodium alkoxide or preferably dimsyl sodium in dimethyl sulfoxide. After about 20 minutes, 0.25 molar equivalents of the compound of formula (9), preferably as a single enantiomer, is added and the mixture stirred at a temperature of about 20°–70° C., preferably about 50° C., for about 1–10 hours, preferably about 4 hours. When the reaction is substantially complete, the product is isolated conventionally. The reaction yields a mixture of the E and Z isomers of the compound of formula (10), which are separated by chromatography to give the E isomer of the compound of formula (10) and the Z isomer of the compound of formula (10).

The reaction of Step 4, in its broadest aspect, comprises reacting a compound of formula (10) with sufficient base to form an ethynyl anion followed by reaction of the anion thus formed with a compound of the formula $R_2R_3CO$, in which $R_2$ and $R_3$ are as defined above, to give a compound of formula (I). In general, the compound of formula (10), as the E isomer or the Z isomer, preferably as a single enantiomer, is reacted with about 3 to 3.5 molar equivalents of an alkyl lithium, preferably n-butyllithium, in order to make the tris-anion of the compound of formula (10). The reaction is carried out in an ethereal solvent as defined above, preferably tetrahydrofuran, at a temperature of about −20° C. to −100° C., preferably about −60° C., for about 30 minutes to 3 hours, preferably about 1 hour. The mixture is then cooled to about −50° C. to −100° C., preferably about −78° C., and about 1 to 1.5 molar equivalents, preferably about 1.1 molar equivalents, of a compound of formula $R_2R_3C=O$ added and the mixture stirred for about 10 minutes to 1 hour, preferably about 20 minutes, at a temperature of about −50° C. to −100° C., preferably about −78° C. When the reaction is substantially complete, the compound of formula (I) is isolated and purified by conventional means.

In an alternative procedure for Step 4, the reaction of the compound of formula (10) with $R_2R_3CO$ is carried out as above but in the presence of an optically active amine, for example (2S,2′S)-2-hydroxymethyl-1-[(1-methylpyrrolidin-2-yl)methyl]pyrrolidine, according to the procedure described in *Chem. Lett.*, (1979), 447, to give either the 3′S- or the 3′R- propargylic alcohol.

The compound of formula (I), as discussed in detail above, may exist as a mixture of stereoisomers. If the starting material of formula (7) in Reaction Scheme IA above is a racemic mixture, a mixture of stereoisomers of formula (I) are obtained as a product, i.e. a mixture of the compounds of formula (Ia), (Ib), (Ic) and (Id) in which all four isomers are either E olefins or all four isomers are Z olefins. If Step 4 is carried out in the presence of a chiral amine a mixture of the compounds of formula (Ia) and (Id), or a mixture of (Ib) and (Ic), is obtained. If the starting material of formula (7) is a single enantiomer, either a mixture of the compounds of formula (Ia) and (Ic) is obtained, or a mixture of the compounds of formula (Ib) and (Id), depending on which enantiomer of formula (7) is used, unless Step 4 is carried out in the presence of a chiral amine, in which case a single stereoisomer of (I) is obtained, i.e. a compound of formula (Ia), (Ib), (Ic) or (Id). The diastereoisomeric mixture of (Ia) and (Ic), (Ib) and (Id), (Ia) and (Id) or (Ib) and (Ic) may then be separated into the individual isomers as their dicobalthexacarbonyl complexes.

The mixture of diastereoisomers, for example (Ia) and (Ic), is first converted to a dicobalthexacarbonyl complex. The mixture of (Ia) and (Ic) is treated with about 1 to 2 molar equivalents, preferably about 1.1 molar equivalents, of dicobalt octacarbonyl in an ethereal solvent as defined above, preferably diethyl ether. The reaction is carried out at a temperature of about 0°–40° C., preferably about 20° C., for about 5 minutes to 2 hours, preferably about 30 minutes. When the reaction is substantially complete the mixture of products is separated conventionally, and the two diastereoisomers separated as their cobalt complexes by chromatography. The cobalt complexes are then converted separately to the stereoisomers of formula (Ia) and (Ic) by reaction with about 1–2 molar equivalents, preferably about 1.2 molar equivalents, of ceric ammonium nitrate in an aqueous solvent, for example acetone-water. The reaction is carried out for about 2 minutes at a temperature of about 25° C. to give the individual compounds of formula (Ia) and (Ic). The mixture of stereoisomers (Ib) and (Id) is also separated in the above manner to give the individual isomers (Ib) and (Id).

The above procedures are discussed in more detail in U.S. Pat. No. 4,608,388, and U.S. patent application Ser. No. 900,025, filed Aug. 25, 1986, the relevant portions of which are hereby incorporated by reference.

An alternative process for the preparation of compounds of formula (I) where $R_2$ is hydrogen is shown in Reaction Scheme IB below.

REACTION SCHEME IB

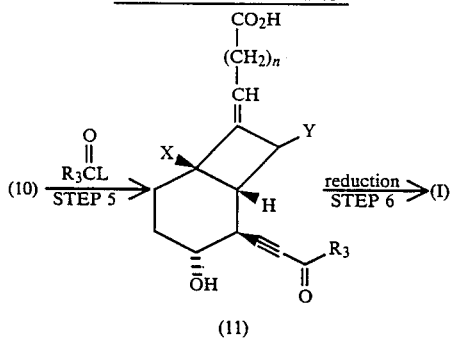

where L is a leaving group.

The reaction of Step 5, in its broadest aspect, comprises reacting an optionally protected compound of formula (10) with sufficient base to form an ethynyl anion followed by reaction of the anion thus formed with a compound of the formula $R_3C(O)L$, in which $R_3$ is as defined above and L is a leaving group, to give a compound of formula (11). Preferably, the compound of formula (10), preferably as a single enantiomer, prepared as shown in Reaction Scheme IA, is reacted in the same manner as described in Reaction Scheme IA with butyllithium to form the tris anion at $-78°$ C. in an ethereal solvent, preferably tetrahydrofuran. About 1 to 1.5 molar equivalents, preferably about 1.1 molar equivalents, of the compound of formula $R_3C(O)L$ in the same solvent is then added, where L is a leaving group, for example halo, lower alkoxy, $R_3C(O)O$, lower alkylthio, or preferably $R_3C(O)L$ is a tertiary amide where L is, for example, morpholino or more preferably N-methoxy-N-methylamino. The preparation of compounds of formula $R_3C(O)L$, where L is N-methoxy-N-methylamino is disclosed in Tetrahedron Letters, Vol. 22 (1981), pp 3815–3818, which is hereby incorporated by reference. The reaction mixture is then stirred for about 10 minutes to 10 hours, at a temperature depending on the leaving group employed. For example, in the case where L is halo, lower alkylthio, $R_3C(O)O$ or lower alkoxy the reaction mixture is allowed to warm to about 0° C., and preferably where L is lower alkoxy or $R_3C(O)O$, boron trifluoride etherate is added to the acetylene anion before reaction with $R_3C(O)L$, according to the procedure disclosed in Tet. Lett., (1984), 2411 and Synthesis, (1986), 421. In the case where L is lower alkylthio the compound of formula (10) is preferably first protected as the trimethylsilyl acetylene derivative then reacted in conjunction with silver fluoroborate in methylene chloride. The reaction is discussed in more detail in Tet. Lett., (1983), 5131. In the case where $R_3C(O)L$ is a tertiary amide the reaction mixture is refluxed until the reaction is complete. When the reaction is substantially complete, the compound of formula (11) is isolated and purified by conventional means.

Other methods of preparing acetylenic ketones are well known in the art, including the reaction of alkynyl trialkyltin derivatives (prepared from the acetylene anion) with acid chlorides (see, for example, Tet. Lett. (1981), 2637), optionally in the presence of a palladium complex (see, for example, J. Org. Chem. (1982), 2549). Another general method is the reaction of trialkylsilyl acetylene derivatives with acid chlorides in the presence of titanium tetrachloride (see, for example, Tet. Lett. (1982), 3203), or through the reaction of acid chlorides with the acetylene in the presence of triethylamine and a palladium complex or with a silyl derivative of the acetylene in the presence of aluminum trichloride (see, for example, J. Org. Chem. (1983), 4887). The methods of preparation of acetylenic ketones given above are provided only to illustrate the types of preparations which are suitable for use in practicing the invention, and are not intended to be exclusive.

The reaction of Step 6, in its broadest aspect, comprises reducing a compound of formula (11), preferably as a single enantiomer, to give a compound of formula (I) where $R_2$ is hydrogen. Single stereoisomers or mixtures of stereoisomers of the compound of formula (I) are obtained depending on the optical purity of the starting compound (11) and the choice of the reducing agent:

(a) Reduction of the compound of formula (11) with a reducing agent such as aluminum hydride, diborane or preferably sodium borohydride leads to a mixture of 3'S-hydroxy and 3'R-hydroxy epimers of the propargyl sidechain. Typically, the ketone of formula (11) is reacted with about 1 to 10 molar equivalents, preferably about 2 to 4 molar equivalents, of sodium borohydride in a protic solvent such as water, ethanol or preferably methanol at a temperature of about 0°–25° C., preferably about 0° C., for about 5 minutes to 4 hours, preferably about 1 hour, giving the compound of formula (I). If the starting ketone of formula (11) in this reduction is a racemic mixture, i.e. prepared from a racemic compound of formula (7) in Reaction Scheme IA above, all four stereoisomers of the compound of formula (I) are obtained as a product, i.e. a mixture of the compounds of formula (Ia), (Ib), (Ic) and (Id), all as the E isomer or all as the Z isomer. If the starting material of formula (11) is a single enantiomer, i.e. prepared from a single enantiomer of formula (7) in Reaction Scheme IB above, either a mixture of the compounds of formula (Ia) and (Ic) is obtained, or a mixture of the compounds of formula (Ib) and (Id), depending on which enantiomer of the compound of formula (7) is used. The diastereoisomeric mixture of (Ia) and (Ic) or (Ib) and (Id) may then be separated into the individual isomers by separation of their cobalt complexes, as described in detail above.

(b) Reduction of the compound of formula (11) with a chiral reducing agent leads to either a 3'S-hydroxy or a 3'R-hydroxy epimer of the propargyl sidechain of the compound of formula (I). For example, reduction of a ketone of formula (11) with isopinocamphenyl-9-borabicyclo[3.3.1]nonane according to the method described in J. Amer. Chem. Soc., 101, 2352 (1979) gives a chiral propargylic alcohol of formula (I) with a 3'S-hydroxy group. An alternative procedure is to use diisocamphenylchloroborane reagent according to the procedure described in J.O.C., 1986, 3394. Yet another procedure is to reduce the ketone of formula (11) with a complex aluminum hydride modified by chiral 2,2'-dihydroxy-1,1'-binaphthyl [preferably (S)-BINAL-H]. See, for example, Tet. Lett., (1981), 247. Thus, if the starting ketone of formula (11) in the chiral reduction is a racemic mixture, i.e. prepared from a racemic compound of formula (7) in Reaction Scheme IA above, a mixture of two stereoisomers of the compound of formula (I) are obtained as a product, i.e. a mixture of the compounds of formula (Ia) and (Id) or a mixture of (Ib) and (Ic), depending upon the chiral reducing agent used. If the starting material of formula (11) is a single enantiomer, i.e. prepared from a single enantiomer of formula (7) in Reaction Scheme IIA above, a single enantiomer of the formula (Ia), (Ib), (Ic) or (Id) is obtained, depending upon which enantiomer of formula (11) is used as a starting material and upon the chiral reducing agent employed.

The preceding discussion of methods of obtaining pure stereoisomers of compounds of formula (I) is not exhaustive, and one of ordinary skill can easily adapt the essential characteristics of the invention to arrive at such stereoisomers without departing from the spirit and scope thereof. For example, mixtures of stereoisomers of the compound of formula (I), as their 3-hydroxy protected derivatives, may be oxidized to the 3-hydroxy protected derivative of the compound of formula (11). The oxidation may be carried out with, for example, a solution of chromic acid in sulfuric acid (Jones reagent), sodium dichromate or an organic chromium reagent, preferably pyridinium chlorochromate. The compound of formula (11) may then be chirally reduced as described above, (as the 3-hydroxy protected or unprotected compound), to give a single stereoisomer of formula (I). Compounds of formula (I) protected at the 3-hydroxy position, preferably as a t-butyldimethylsilyl derivative, may be prepared by first protecting the 3-hydroxy group of the compound of formula (10) and then following the procedure of Reaction Scheme IA.

Preparation of Starting Materials

The phosphorus ylides (Wittig reagents) are prepared by procedures well known in the chemical arts, for example by reaction of the appropriate ω-halocarboxylic acid with triphenylphosphine to give the corresponding triphenylphosphonium salt, which is reacted with a base. The reaction is discussed in more detail in *J. Org. Chem.* 27, 3404 (1962), which is incorporated herein by reference.

The following examples serve to illustrate the invention. They should not be construed as in any way narrowing or limiting the scope of the invention as claimed.

PREPARATION 1

Preparation of 8,8-dichlorobicyclo[4.2.0]oct-2-en-7-one (2) and related compounds of formula (2B) and (2C)

A. A mixture of 34.0 g of cyclohexadiene and 35.0 g of dichloroacetyl chloride in 300 ml of diethyl ether under nitrogen was refluxed while adding 31.5 g of triethylamine dropwise over a period of 3 hours. The mixture was then stirred at room temperature for 20 hours and filtered. The filtrate was washed with brine, 1N hydrochloric acid, saturated sodium bicarbonate and then dried over anhydrous sodium sulfate. The solvent was removed under reduced pressure and the residue distilled to give 32 g of 8,8-dichlorobicyclo[4.2.0]oct-2-en-7-one.

B. Similarly, starting from 2-chloropropionyl chloride in place of dichloroacetyl chloride, the following mixture of compounds of formula (2B) and (2C) was obtained:
8-endo-chloro-8-exo-methylbicyclo[4.2.0]oct-2-en-7-one; and
8-exo-chloro-8-endo-methylbicyclo[4.2.0]oct-2-en-7-one,
which were separated by chromatography on silica gel, eluting with a mixture of methylene chloride and hexane (1:1).

C. Similarly, starting with the appropriate 2-chloroalkanoyl chloride in place of 2-chloropropionyl chloride in preparation 1.A. above, the following mixtures of compounds of formula (2B) and (2C) are prepared:
8-exo-chloro-8-endo-ethylbicyclo[4.2.0]oct-2-en-7-one, and
8-endo-chloro-8-exo-ethylbicyclo[4.2.0]oct-2-en-7-one;
8-exo-chloro-8-endo-n-butylbicyclo[4.2.0]oct-2-en-7-one; and
8-endo-chloro-8-exo-n-butylbicyclo[4.2.0]oct-2-en-7-one.

PREPARATION 2

Preparation of bicyclo[4.2.0]oct-2-en-7-one

A. To a solution of 1.1 g of 8,8-dichlorobicyclo[4.2.0]oct-2-en-7-one in 10 ml of glacial acetic acid was added 2.0 g of zinc dust in portions over a period of 15 minutes. The mixture was then stirred at 65° C. for 1 hour, then a further 0.5 g of zinc dust was added and the mixture stirred at 75° C. for 1 hour. The mixture was cooled, filtered, the solid washed with hexane, the filtrate and combined washings diluted with water and extracted with hexane. The hexane layer was dried over anhydrous sodium sulfate, the solvent removed under reduced pressure and the residue distilled under vacuum to give 500 mg of bicyclo[4.2.0]oct-2-en-7-one, the compound of formula (III), where X and Y are hydrogen.

B. Similarly, starting with (1S,6R)- or (1R,6S)-8,8-dichlorobicyclo[4.2.0]oct-2-en-7-one in place of the racemic compound in 2.A. above, (1S,6R)- or (1R,6S)-bicyclo[4.2.0]oct-2-en-7-one was prepared.

C. Similarly, starting with racemic 8-endo-chloro-8-exo-methyl- or 8-exo-chloro-8-endo-methylbicyclo[4.2.0]oct-2-en-7-one in place of 8,8-dichlorobicyclo[4.2.0]oct-2-en-7-one, 8-exo- or 8-endo-methylbicyclo[4.2.0]oct-2-en-7-one is prepared. Similarly, starting with (1S,6R)- or (1R,6S)-8-endo-chloro-8-exo-methylbicyclo[4.2.0]oct-2-en-7-one or (1S,6R)- or (1R,6S)-8-exo-chloro-8-endo-methyl-bicyclo[4.2.0]oct-2-en-7-one, in place of the racemic compound in 2.A. above, (1S,6R)- or (1R,6S)-8-endo-methylbicyclo[4.2.0]oct-2-en-7-one or 8-exo-methylbicyclo[4.2.0]oct-2-en-7-one is prepared.

PREPARATION 3

Preparation of 6-methoxybicyclo[4.2.0]oct-2-en-7-one and related compounds of formula (3) where Y is Hydrogen A. To a stirred solution of 60 g of 8,8-dichlorobicyclo[4.2.0]oct-2-en-7-one, prepared as shown in Preparation 1, in 500 ml of methanol under nitrogen at room temperature was added 48 ml of triethylamine over a period of 1 hour. The mixture was stirred for 30 minutes, then 90 g of ammonium chloride and 60 g of zinc-copper couple (as a powder) was added. The reaction mixture was stirred at room temperature for 2.5 hours, filtered through Celite and the solvent removed under reduced pressure. The residue was dissolved in ethyl acetate, washed with brine, dried over anhydrous sodium sulfate and the solvent was distilled under vacuum, giving 32 g of 6-methoxybicyclo[4.2.0]oct-2-en-7-one.

B. Similarly, starting with (1S,6R)-8,8-dichlorobicyclo[4.2.0]oct-2-en-7-one in place of the racemic compound in Preparation 3.A. above, (1S,6S)-6-methoxybicyclo[4.2.0]oct-2-en-7-one is prepared. Similarly, starting with the (1R,6S)-compound, (1R,6R)-6-methoxybicyclo[4.2.0]oct-2-en-7-one is prepared.

C. Similarly, replacing methanol in Preparation 3.A. above with the appropriate alcohol, the following exemplary compounds of formula (3) where Y is H are made:
6-ethoxybicyclo[4.2.0]oct-2-en-7-one;
6-propoxybicyclo[4.2.0]oct-2-en-7-one;
6-butoxybicyclo[4.2.0]oct-2-en-7-one; and
6-isobutoxybicyclo[4.2.0]oct-2-en-7-one.

PREPARATION 4

Preparation of
6-methoxy-8-endo-methylbicyclo[4.2.0]oct-2-en-7-one and related compounds of formula (3) where Y is lower alkyl A. A solution of 1.0 g of 8-exo-chloro-8-endo-methylbicyclo[4.2.0]oct-2-en-7-one, prepared as shown in Preparation 2B, in 100 ml of methanol was stirred at room temperature while adding 0.6 ml of triethylamine dropwise over a period of 1 hour. Stirring was continued for a further 15 minutes then methanol was removed from the mixture under reduced pressure. The residue was partitioned between diethyl ether and brine solution and the organic layer dried over anhydrous sodium sulfate. Solvent was removed from the filtrate under reduced pressure, and the residue chromatographed on silica gel, eluting with 12% ethyl acetate in hexane, to give 830 mg of 6-methoxy-8-endo-methylbicyclo[4.2.0]oct-2-en-7-one.

B. Similarly, replacing 8-exo-chloro-8-endo-methylbicyclo[4.2.0]oct-2-en-7-one with the 8-exo-methyl isomer in paragraph 4.A. above, the corresponding compound of formula (3) was prepared i.e. 6-methoxy-8-exo-methylbicyclo[4.2.0]-oct-2-en-7-one.

C. Similarly, starting with (1S,6R)-8-exo-chloro-8-endo-methylbicyclo[4.2.0]oct-2-en-7-one the optically active compound (1R,6S)-6-methoxy-8-endo-methylbicyclo[4.2.0]oct-2-en-7-one is prepared, and starting with the (1R,6S)-isomer, (1S,6R)-6-methoxy-8-endo-methylbicyclo[4.2.0]oct-2-en-7-one is prepared.

Similarly, (1R,6S)-6-methoxy-8-exo-methyl-bicyclo[4.2.0]oct-2-en-7-one and (1S,6R)-6-methoxy-8-exo-methylbicyclo[4.2.0]oct-2-en-7-one are prepared.

D. Similarly, replacing 8-exo-chloro-8-endo-methylbicyclo[4.2.0]oct-2-en-7-one with the appropriate compound of formula (2B) or (2C), the following exemplary compounds of formula (3) where Y is exo- or endo-(lower alkyl) are prepared:
6-ethoxy-8-methylbicyclo[4.2.0]oct-2-en-7-one;
6-propoxy-8-methylbicyclo[4.2.0]oct-2-en-7-one;
6-n-butoxy-8-methylbicyclo[4.2.0]oct-2-en-7-one;
6-isobutoxy-8-methylbicyclo[4.2.0]oct-2-en-7-one;
6-methoxy-8-ethylbicyclo[4.2.0]oct-2-en-7-one;
6-methoxy-8-n-butylbicyclo[4.2.0]oct-2-en-7-one; and
6-n-butoxy-8-n-butylbicyclo[4.2.0]oct-2-en-7-one.

PREPARATION 5

Preparation of
spiro[bicyclo[4.2.0]oct-2-ene-7,2″-(1″,3″-dioxolane)] and related compounds of formula (4)

A. A mixture of 6.4 g of bicyclo[4.2.0]oct-2-en-7-one (3), 18.62 g of ethylene glycol, 100 ml of benzene, and 25 mg of p-toluenesulfonic acid was heated at reflux for 4 hr using a Dean-Stark trap to effect continuous removal of water. The cooled reaction mixture was poured on to 100 ml saturated sodium bicarbonate solution and the resulting mixture extracted with three 75 ml portions of diethyl ether. The combined organic extract was washed with 100 ml saturated sodium chloride solution and then dried over sodium sulfate. The solvent was removed under vacuum and the residue distilled under vacuum to give 7.12 g of spiro[bicyclo[4.2.0]oct-2-ene-7,2″-(1″,3″-dioxolane)] (4).

B. Similarly, following the procedure of paragraph 5.A. above, replacing bicyclo[4.2.0]oct-2-en-7-one with the appropriate compounds of formula (3) the following compounds of formula (4) were prepared:
Spiro[6-methoxybicyclo[4.2.0]oct-2-ene-7,2″-(1″,3″-dioxolane)];
Spiro[6-methoxy-8-exo-methylbicyclo[4.2.0]oct-2-ene-7,2″-(1″,3″-dioxolane)]; and
Spiro[6-methoxy-8-endo-methylbicyclo[4.2.0]oct-2-ene-7,2″-(1″,3″-dioxolane)].

C. Similarly, following the procedure of paragraph 5.A. above, replacing bicyclo[4.2.0]oct-2-en-7-one with the appropriate optically active compounds, prepared as shown in Preparations 3.B. and 4.C., the following exemplary enantiomers of compounds of formula (4) are prepared:
(1S,6S)-Spiro[6-methoxybicyclo[4.2.0]oct-2-ene-7,2″-(1″,3″-dioxolane)]
(1R,6R)-Spiro[6-methoxybicyclo[4.2.0]oct-2-ene-7,2″-(1″,3″-dioxolane)]
(1S,6R)-Spiro[6-methoxy-8-exo-methylbicyclo[4.2.0]oct-2-ene-7,2″-(1″,3″-dioxolane)]
(1R,6S)-Spiro[6-methoxy-8-exo-methylbicyclo[4.2.0]oct-2-ene-7,2″-(1″,3″-dioxolane)]
(1S,6R)-Spiro[6-methoxy-8-endo-methylbicyclo[4.2.0]oct-2-ene-7,2″-(1″,3″-dioxolane)]
(1R,6S)-Spiro[6-methoxy-8-endo-methylbicyclo[4.2.0]oct-2-ene-7,2″-(1″,3″-dioxolane)]

D. Similarly, following the procedures of paragraph 5.A. above, the following representative compounds of formula (4) where Y is hydrogen are prepared:
Spiro[6-ethoxybicyclo[4.2.0]oct-2-ene-7,2″-(1″,3″-dioxolane)];
Spiro[6-propoxybicyclo[4.2.0]oct-2-ene-7,2″-(1″,3″-dioxolane)];
Spiro[6-butoxybicyclo[4.2.0]oct-2-ene-7,2″-(1″,3″-dioxolane)]; and
Spiro[6-isobutoxybicyclo[4.2.0]oct-2-ene-7,2″-(1″,3″-dioxolane)].

E. Similarly, following the procedures of paragraph 5.A. above, the following representative compounds of formula (4), where Y is exo or endo-(lower alkyl), are prepared.
Spiro[6-ethoxy-8-methylbicyclo[4.2.0]oct-2-ene-7,2″-(1″,3″-dioxolane)];
Spiro[6-propoxy-8-methylbicyclo[4.2.0]oct-2-ene-7,2″-(1″,3″-dioxolane)];
Spiro[6-n-butoxy-8-methylbicyclo[4.2.0]oct-2-ene-7,2″-(1″,3″-dioxolane)];
Spiro[8-methylbicyclo[4.2.0]oct-2-ene-7,2″-(1″,3″-dioxolane)].
Spiro[8-n-butylbicyclo[4.2.0]oct-2-ene-7,2″-(1″,3″-dioxolane)];
Spiro[6-methoxy-8-ethylbicyclo[4.2.0]oct-2-ene-7,2″-(1″,3″-dioxolane)];
Spiro[6-methoxy-8-n-butylbicyclo[4.2.0]oct-2-ene-7,2″-(1″,3″-dioxolane)]; and
Spiro[6-n-butoxy-8-n-butylbicyclo[4.2.0]oct-2-ene-7,2″-(1″,3″-dioxolane)].

PREPARATION 6

Preparation of
(1SR,2SR,3RS,6SR)-Spiro[2,3-epoxybicyclo[4.2.0]octane-7,2″-(1″,3″-dioxolane)] and
(1SR,2RS,3SR,6SR)-Spiro[2,3-epoxybicyclo[4.2.0]octane-7,2″-(1″,3″-dioxolane)] and related compounds of formulas (6) and (7)

A. To a stirred solution of 5 g of spiro[bicyclo[4.2.0]oct-2-ene-7,2″-(1″,3″-dioxolane)], prepared according to Preparation 5, in 40 ml acetone and 20 ml water at 0° C. was added 4.76 g of N-bromoacetamide over 1 hour. This mixture was stirred at room temperature for 20 hours. To this solution was added 12.4 g potassium carbonate and the resulting mixture was stirred at room temperature for 3 days. The mixture was saturated with sodium chloride and the resulting mixture extracted with four 150 ml portions of diethyl ether. The combined organic extract was washed with 100 ml of saturated sodium chloride solution and dried over sodium sulfate. Removal of solvent in vacuum and chromatographic purification of the residue on silica gel eluting with 15% ethyl acetate-hexane gave 3.45 g of a ca. 4:1 mixture of (1SR,2SR,3RS,6SR)-Spiro[2,3-epoxybicyclo[4.2.0]octane-7,2″-(1″,3″-dioxolane)] and (1SR,2RS,3SR,6SR)-Spiro[2,3-epoxybicyclo[4.2.0]octane-7,2″-(1″,3″-dioxolane)].

B. Similarly, starting with the appropriate compounds of formula (4) in place of spiro[bicyclo[4.2.0]oct-2-ene-7,2″-(1″,3″-dioxolane)] and following the procedures of paragraph 6.A. above, the following mixtures of compounds of formula (6) and (7) were prepared:
(1RS,2SR,3RS,6RS)-Spiro[2,3-epoxy-6-methoxybicyclo[4.2.0]octane-7,2″-(1″,3″-dioxolane)], and
(1RS,2RS,3SR,6RS)-Spiro[2,3-epoxy-6-methoxybicyclo[4.2.0]octane-7,2″-(1″,3″-dioxolane)];
(1RS,2SR,3RS,6RS)-Spiro[2,3-epoxy-6-methoxy-8-exo-methylbicyclo[4.2.0]octane-7,2″-(1″,3″-dioxolane)], and
(1RS,2RS,3SR,6RS)-Spiro[2,3-epoxy-6-methoxy-8-exo-methylbicyclo[4.2.0]octane-7,2″-(1″,3″-dioxolane)];
(1RS,2SR,3RS,6RS)-Spiro[2,3-epoxy-6-methoxy-8-endo-methylbicyclo[4.2.0]octane-7,2″-(1″,3″-dioxolane)], and
(1RS,2RS,3SR,6RS)-Spiro[2,3-epoxy-6-methoxy-8-endo-methylbicyclo[4.2.0]octane-7,2″-(1″,3″-dioxolane)].

C. Similarly, starting with the appropriate enantiomers of compounds of formula (4), prepared as shown in Preparation 5.C., in place of spiro[bicyclo[4.2.0]oct-2-ene-7,2″-(1″,3″-dioxolane)] and following the procedures of paragraph 6A above, the following exemplary mixtures of enantiomers of compounds of formula (6) and (7) are prepared:
(1R,2R,3S,6R)- and (1R,2S,3R,6R)-Spiro-[2,3-epoxybicyclo[4.2.0]octane-7,2″-(1″,3″-dioxolane)].
(1S,2S,3R,6S)- and (1S,2R,3S,6S)-Spiro-[2,3-epoxybicyclo[4.2.0]octane-7,2″-(1″,3″-dioxolane)].
(1S,2R,3S,6S)- and (1S,2S,3R,6S)-Spiro-[2,3-epoxy-6-methoxybicyclo[4.2.0]octane-7,2″-(1″,3″-dioxolane)].
(1R,2S,3R,6R)- and (1R,2R,3S,6R)-Spiro-[2,3-epoxy-6-methoxybicyclo[4.2.0]octane-7,2″-(1″,3″-dioxolane)].
(1S,2R,3S,6S)- and (1S,2S,3R,6S)-Spiro-[2,3-epoxy-6-methoxy-8-exo-methylbicyclo[4.2.0]octane-7,2″-(1″,3″-dioxolane)].
(1R,2S,3R,6R)- and (1R,2R,3S,6R)-Spiro-[2,3-epoxy-6-methoxy-8-exo-methylbicyclo[4.2.0]octane-7,2″-(1″,3″-dioxolane)].
(1S,2R,3S,6S)- and (1S,2S,3R,6S)-Spiro-[2,3-epoxy-6-methoxy-8-endo-methylbicyclo[4.2.0]octane-7,2″-(1″,3″-dioxolane)].
(1R,2S,3R,6R)- and (1R,2R,3S,6R)-Spiro-[2,3-epoxy-6-methoxy-8-endo-methylbicyclo[4.2.0]octane-7,2″-(1″,3″-dioxolane)].

D. Similarly, following the procedures of 6.A. above, the following exemplary mixtures of compounds of formula (6) and (7) are prepared:
(1RS,2SR,3RS,6RS)-Spiro[2,3-epoxy-6-ethoxybicyclo[4.2.0]octane-7,2″-(1″,3″-dioxolane)], and
(1RS,2RS,3SR,6RS)-Spiro[2,3-epoxy-6-ethoxybicyclo[4.2.0]octane-7,2″-(1″,3″-dioxolane)];
(1RS,2SR,3RS,6RS)-Spiro[2,3-epoxy-6-n-butoxybicyclo[4.2.0]octane-7,2″-(1″,3″-dioxolane)];
(1RS,2RS,3SR,6RS)-Spiro[2,3-epoxy-6-n-butoxybicyclo[4.2.0]octane-7,2″-(1″,3″-dioxolane)];
(1RS,2SR,3RS,6RS)-Spiro[2,3-epoxy-6-isobutoxybicyclo[4.2.0]octane-7,2″-(1″,3″-dioxolane)];
(1RS,2RS,3SR,6RS)-Spiro[2,3-epoxy-6-isobutoxybicyclo[4.2.0]octane-7,2″-(1″,3″-dioxolane)];
(1SR,2SR,3RS,6SR)-Spiro[2,3-epoxy-8-endo-methylbicyclo[4.2.0]octane-7,2″-(1″,3″-dioxolane)], and
(1SR,2RS,3SR,6SR)-Spiro[2,3-epoxy-8-endo-methylbicyclo[4.2.0]octane-7,2″-(1″,3″-dioxolane)];
(1SR,2SR,3RS,6SR)-Spiro[2,3-epoxy-8-exo-ethylbicyclo[4.2.0]octane-7,2″-(1″,3″-dioxolane)], and
(1SR,2RS,3SR,6SR)-Spiro[2,3-epoxy-8-exo-ethylbicyclo[4.2.0]octane-7,2″-(1″,3″-dioxolane)];
(1SR,2SR,3RS,6SR)-Spiro[2,3-epoxy-8-endo-n-butylbicyclo[4.2.0]octane-7,2″-(1″,3″-dioxolane)], and
(1SR,2RS,3SR,6SR)-Spiro[2,3-epoxy-8-endo-n-butylbicyclo[4.2.0]octane-7,2″-(1″,3″-dioxolane)];
(1RS,2SR,3RS,6RS)-Spiro[2,3-epoxy-6-ethoxy-8-exo-methylbicyclo[4.2.0]octane-7,2″-(1″,3″-dioxolane)], and
(1RS,2RS,3SR,6RS)-Spiro[2,3-epoxy-6-ethoxy-8-exo-methylbicyclo[4.2.0]octane-7,2″-(1″,3″-dioxolane)];
(1RS,2SR,3RS,6RS)-Spiro[2,3-epoxy-6-n-butoxy-8-endomethylbicyclo[4.2.0]octane-7,2″-(1″,3″-dioxolane)], and
(1RS,2RS,3SR,6RS)-Spiro[2,3-epoxy-6-n-butoxy-8-endomethylbicyclo[4.2.0]octane-7,2″-(1″,3″-dioxolane)];
(1RS,2SR,3RS,6RS)-Spiro[2,3-epoxy-6-methoxy-8-exo-ethylbicyclo[4.2.0]octane-7,2″-(1″,3″-dioxolane)], and
(1RS,2RS,3SR,6RS)-Spiro[2,3-epoxy-6-methoxy-8-exo-ethylbicyclo[4.2.0]octane-7,2″-(1″,3″-dioxolane)];
(1RS,2SR,3RS,6RS)-Spiro[2,3-epoxy-6-methoxy-8-endo-n-butylbicyclo[4.2.0]octane-7,2″-(1″,3″-dioxolane)], and
(1RS,2RS,3SR,6RS)-Spiro[2,3-epoxy-6-methoxy-8-endo-n-butylbicyclo[4.2.0]octane-7,2″-(1″,3″-dioxolane)];
(1RS,2SR,3RS,6RS)-Spiro[2,3-epoxy-6-n-butoxy-8-exo-n-butylbicyclo[4.2.0]octane-7,2″-(1″,3″-dioxolane)], and
(1RS,2RS,3SR,6RS)-Spiro[2,3-epoxy-6-n-butoxy-8-exo-n-butylbicyclo[4.2.0]octane-7,2″-(1″,3″-dioxolane)].

PREPARATION 7

Alternative preparation of
(1RS,2SR,3RS,6RS)-Spiro[2,3-epoxy-6-methoxybicyclo[4.2.0]octane-7,2''-(1'',3''-dioxolane)] and
(1RS,2RS,3SR,6RS)-Spiro[2,3-epoxy-6-methoxybicyclo[4.2.0]octane-7,2''-(1'',3''-dioxolane)] and related compounds of formulas (6) and (7)

A. A mixture of 5.4 g of spiro[6-methoxybicyclo[4.2.-0]oct-2-ene-7,2''-(1'',3''-dioxolane)] and 5.5 g of m-chloroperbenzoic acid in 80 ml of dichloromethane was stirred at room temperature for 3 hours. The mixture was then washed with aqueous sodium bicarbonate solution, dried over anhydrous sodium sulfate and the solvent removed under reduced pressure. The residue was chromatographed on silica gel, eluting with ethyl acetatehexane (1:1) to give a mixture of the endo and exo epoxides in a 2:1 ratio, namely:

(1RS,2SR,3RS,6RS)-spiro[2,3-epoxy-6-methoxybicyclo[4.2.0]octane-7,2''-(1'',3''-dioxolane)] and
(1RS,2RS,3SR,6RS)-spiro[2,3-epoxy-6-methoxybicyclo[4.2.0]octane-7,2''-(1'',3''-dioxolane)];

B. Similarly, starting with the appropriate enantiomers of compounds of formula (4), prepared as shown in Preparation 5.C., in place of spiro[6-methoxybicyclo[4.2.0]oct-2-ene-7,2''-(1'',3''-dioxolane)] and following the procedures of paragraph 7.A. above, the following exemplary mixtures of enantiomers of compounds of formula (6) and (7) are prepared:

(1S,2R,3S,6S)- and (1S,2S,3R,6S)-Spiro-[2,3-epoxy-6-methoxybicyclo[4.2.0]octane-7,2''-(1'',3''-dioxolane)].
(1R,2S,3R,6R)- and (1R,2R,3S,6R)-Spiro-[2,3-epoxy-6-methoxybicyclo[4.2.0]octane-7,2''-(1'',3''-dioxolane)].
(1S,2R,3S,6S)- and (1S,2S,3R,6S)-Spiro-[2,3-epoxy-6-methoxy-8-exo-methylbicyclo[4.2.0]octane-7,2''-(1'',3''-dioxolane)].
(1R,2S,3R,6R)- and (1R,2R,3S,6R)-Spiro-[2,3-epoxy-6-methoxy-8-exo-methylbicyclo[4.2.0]octane-7,2''-(1'',3''-dioxolane)].
(1S,2R,3S,6S)- and (1S,2S,3R,6S)-Spiro-[2,3-epoxy-6-methoxy-8-endo-methylbicyclo[4.2.0]octane-7,2''-(1'',3''-dioxolane)].
(1R,2S,3R,6R)- and (1R,2R,3S,6R)-Spiro-[2,3-epoxy-6-methoxy-8-endo-methylbicyclo[4.2.0]octane-7,2''-(1'',3''-dioxolane)].

C. Similarly, starting with the appropriate compounds of formula (4) in place of spiro[6-methoxybicyclo[4.2.0]oct-2-ene-7,2''-(1'',3''-dioxolane)] and following the procedures of paragraph 7.A. above, the following exemplary mixtures of compounds of formula (6) and (7) where Y is hydrogen, or exo or endo-(lower alkyl) are prepared:

(1RS,2SR,3RS,6RS)-Spiro[2,3-epoxy-6-(2,2,2-trifluoroethoxy)bicyclo[4.2.0]octane-7,2''-(1'',3''-dioxolane)], and
(1RS,2RS,3SR,6RS)-Spiro[2,3-epoxy-6-(2,2,2-trifluoroethoxy)bicyclo[4.2.0]octane-7,2''-(1'',3''-dioxolane)];
(1RS,2SR,3RS,6RS)-Spiro[2,3-epoxy-6-methoxy-8-methylbicyclo[4.2.0]octane-7,2''-(1'',3''-dioxolane)], and
(1RS,2RS,3SR,6RS)-Spiro[2,3-epoxy-6-methoxy-8-methylbicyclo[4.2.0]octane-7,2''-(1'',3''-dioxolane)];
(1RS,2SR,3RS,6RS)-Spiro[2,3-epoxy-6-ethoxybicyclo[4.2.0]octane-7,2''-(1'',3''-dioxolane)], and
(1RS,2RS,3SR,6RS)-Spiro[2,3-epoxy-6-ethoxybicyclo[4.2.0]octane-7,2''-(1'',3''-dioxolane)];
(1RS,2SR,3RS,6RS)-Spiro[2,3-epoxy-6-n-butoxybicyclo[4.2.0]octane-7,2''-(1'',3''-dioxolane)]; and
(1RS,2RS,3SR,6RS)-Spiro[2,3-epoxy-6-n-butoxybicyclo[4.2.0]octane-7,2''-(1'',3''-dioxolane)];
(1RS,2SR,3RS,6RS)-Spiro[2,3-epoxy-6-isobutoxybicyclo[4.2.0]octane-7,2''-(1'',3''-dioxolane)], and
(1RS,2RS,3SR,6RS)-Spiro[2,3-epoxy-6-isobutoxybicyclo[4.2.0]octane-7,2''-(1'',3''-dioxolane)];
(1RS,2SR,3RS,6RS)-Spiro[2,3-epoxy-6-(2,2,2-trifluoroethoxy)-8-methylbicyclo[4.2.0]octane-7,2''-(1'',3''-dioxolane)], and
(1RS,2RS,3SR,6RS)-Spiro[2,3-epoxy-6-(2,2,2-trifluoroethoxy)-8-methylbicyclo[4.2.0]octane-7,2''-(1'',3''-dioxolane)];
(1RS,2SR,3RS,6RS)-Spiro[2,3-epoxy-6-ethoxy-8-methylbicyclo[4.2.0]octane-7,2''-(1'',3''-dioxolane)], and
(1RS,2RS,3SR,6RS)-Spiro[2,3-epoxy-6-ethoxy-8-methylbicyclo[4.2.0]octane-7,2''-(1'',3''-dioxolane)];
(1RS,2SR,3RS,6RS)-Spiro[2,3-epoxy-6-n-butoxy-8-methylbicyclo[4.2.0]octane-7,2''-(1'',3''-dioxolane)], and
(1RS,2RS,3SR,6RS)-Spiro[2,3-epoxy-6-n-butoxy-8-methylbicyclo[4.2.0]octane-7,2''-(1'',3''-dioxolane)];
(1RS,2SR,3RS,6RS)-Spiro[2,3-epoxy-6-methoxy-8-ethylbicyclo[4.2.0]octane-7,2''-(1'',3''-dioxolane)], and
(1RS,2RS,3SR,6RS)-Spiro[2,3-epoxy-6-methoxy-8-ethylbicyclo[4.2.0]octane-7,2''-(1'',3''-dioxolane)];
(1RS,2SR,3RS,6RS)-Spiro[2,3-epoxy-6-methoxy-8-n-butylbicyclo[4.2.0]octane-7,2''-(1'',3''-dioxolane)], and
(1RS,2RS,3SR,6RS)-Spiro[2,3-epoxy-6-methoxy-8-n-butylbicyclo[4.2.0]octane-7,2''-(1'',3''-dioxolane)];
(1RS,2SR,3RS,6RS)-Spiro[2,3-epoxy-6-n-butoxy-8-n-butylbicyclo[4.2.0]octane-7,2''-(1'',3''-dioxolane)], and
(1RS,2RS,3SR,6RS)-Spiro[2,3-epoxy-6-n-butoxy-8-n-butylbicyclo[4.2.0]octane-7,2''-(1'',3''-dioxolane)].

PREPARATION 8

Preparation of the mixture of
(1RS,2SR,3RS,6SR)-Spiro[2-ethynyl-3-hydroxybicyclo[4.2.0]octane-7,2''-(1'',3''-dioxolane)] and Related Compounds of Formula (8)

A. A solution of 41.5 ml of 1.28M n-butyllithium in hexane in 60 ml of tetrahydrofuran under nitrogen was cooled to −78° C. and acetylene bubbled through the stirred solution. After 90 minutes the acetylene flow was stopped and 6.0 g of a mixture of (1SR,2SR,3RS,6SR)-Spiro[2,3-epoxybicyclo[4.2.0]octane-7,2''-(1'',3''-dioxolane)] and (1SR,2RS,3SR,6SR)-Spiro[2,3-epoxybicyclo[4.2.0]-octane-7,2''-(1'',3''-dioxolane)] in 20 ml of tetrahydrofuran added dropwise, followed by 4.7 ml of boron trifluoride etherate. After stirring for 1 hour excess aqueous sodium sulfate was added, and the resulting mixture was warmed to room temperature and extracted thoroughly with ethyl acetate. This extract was dried over sodium sulfate, solvent removed from the filtrate under reduced pressure and the residue chromatographed on silica gel, eluting with 30% acetone in methylene chloride to give (1RS,2SR,3RS,6SR)-Spiro[2-ethynyl-3-hydroxybicyclo[4.2.0]octane-7,2''-(1'',3''-dioxolane)]

B. In like manner, following the procedure of paragraph 8.A. above, but replacing the racemic mixture of epoxides with a mixture of one enantiomer of the compounds of formula (6) and (7), prepared as shown in Preparations 6.C. and 7.B., the following exemplary enantiomers of compounds of formula (8) are prepared:

(1R,2S,3R,6S)-Spiro[2-ethynyl-3-hydroxybicyclo[4.2.0]octane-7,2″-(1″,3″-dioxolane)];
(1S,2R,3S,6R)-Spiro[2-ethynyl-3-hydroxybicyclo[4.2.0]octane-7,2″-(1″,3″-dioxolane)];
(1S,2S,3R,6S)-Spiro[2-ethynyl-3-hydroxy-8-endo-methylbicyclo[4.2.0]octane-7,2″-(1″,3″-dioxolane)];
(1R,2R,3S,6R)-Spiro[2-ethynyl-3-hydroxy-8-endo-methylbicyclo[4.2.0]octane-7,2″-(1″,3″-dioxolane)];
(1R,2S,3R,6R)-Spiro[2-ethynyl-3-hydroxy-6-methoxybicyclo[4.2.0]octane-7,2″-(1″,3″-dioxolane)];
(1S,2R,3S,6S)-Spiro[2-ethynyl-3-hydroxy-6-methoxybicyclo[4.2.0]octane-7,2″-(1″,3″-dioxolane)];
(1S,2S,3R,6R)-Spiro[2-ethynyl-3-hydroxy-6-methoxy-8-exo-methylbicyclo[4.2.0]octane-7,2″-(1″,3″-dioxolane)];
(1R,2R,3S,6S)-Spiro[2-ethynyl-3-hydroxy-6-methoxy-8-exo-methylbicyclo[4.2.0]octane-7,2″-(1″,3″-dioxolane)];
(1S,2S,3R,6R)-Spiro[2-ethynyl-3-hydroxy-6-methoxy-8-endo-methylbicyclo[4.2.0]octane-7,2″-(1″,3″-dioxolane)];
(1R,2R,3S,6S)-Spiro[2-ethynyl-3-hydroxy-6-methoxy-8-endo-methylbicyclo[4.2.0]octane-7,2″-(1″,3″-dioxolane)];

C. In like manner, following the procedure of paragraph 8.A. above, but replacing the mixture of epoxides with other mixtures of compounds of formula (6) and (7), the following mixtures of compounds of formula (8) where Y is hydrogen, or exo- or endo-(lower alkyl), are prepared:

(1RS,2SR,3RS,6RS)-spiro[2-ethynyl-3-hydroxy-6-methoxybicyclo[4.2.0]octane-7,2″-(1″,3″-dioxolane)];
(1SR,2SR,3RS,6SR)-spiro[2-ethynyl-3-hydroxy-8-endo-methylbicyclo[4.2.0]octane-7,2″-(1″,3″-dioxolane)];
(1SR,2SR,3RS,6RS)-spiro-[2-ethynyl-3-hydroxy-6-methoxy-8-exo-methylbicyclo[4.2.0]octane-7,2″-(1″,3″-dioxolane)];
(1SR,2SR,3RS,6RS)-spiro-[2-ethynyl-3-hydroxy-6-methoxy-8-endo-methylbicyclo[4.2.0]octane-7,2″-(1″,3″-dioxolane)]
(1RS,2SR,3RS,6RS)-spiro-[2-ethynyl-3-hydroxy-6-ethoxybicyclo[4.2.0]octane-7,2″-(1″,3″-dioxolane)];
(1RS,2SR,3RS,6RS)-spiro-[2-ethynyl-3-hydroxy-6-n-butoxybicyclo[4.2.0]octane-7,2″-(1″,3″-dioxolane)];
(1SR,2SR,3RS,6RS,)-spiro-[2-ethynyl-3-hydroxy-6-ethoxy-8-methylbicyclo[4.2.0]octane-7,2″-(1″,3″-dioxolane)];
(1SR,2SR,3RS,6RS,)-spiro-[2-ethynyl-3-hydroxy-6-methoxy-8-ethylbicyclo[4.2.0]octane-7,2″-(1″,3″-dioxolane)];
(1SR,2SR,3RS,6RS,)-spiro-[2-ethynyl-3-hydroxy-6-methoxy-8-n-butylbicyclo[4.2.0]octane-7,2″-(1″,3″-dioxolane)];
(1SR,2SR,3RS,6RS,)-spiro-[2-ethynyl-3-hydroxy-6-butoxy-8-n-butylbicyclo[4.2.0]octane-7,2″-(1″,3″-dioxolane)];

PREPARATION 9

Preparation of (1RS,2SR,3RS,6SR)-2-ethynyl-3-hydroxybicyclo[4.2.0]octan-7-one and Related Compounds of Formulas (9).

A. A solution of 2.5 g of (1RS,2SR,3RS,6SR)-Spiro[2-ethynyl-3-hydroxybicyclo[4.2.0]octane-7,2″-(1″,3″-dioxolane)], prepared as shown in Preparation 8 in 50 ml of acetonitrile and 17 ml of 0.5 N sulfuric acid was stirred at 25° C. for 16 hours. The reaction was quenched by neutralization with aqueous sodium bicarbonate and the mixture was extracted with diethyl ether. The extracts were dried with magnesium sulfate and evaporated to dryness to give (1RS,2SR,3RS,6SR)-2-ethynyl-3-hydroxybicyclo[4.2.0]octan-7-one.

B. In like manner, following the procedure of paragraph 9.A. above, but replacing (1RS,2SR,3RS,6SR)-Spiro[2-ethynyl-3-hydroxybicyclo[4.2.0]octane-7,2″-(1″,3″-dioxolane)] with a single enantiomer of formula (8), prepared as shown in Preparation 8.B., the following exemplary enantiomers of compounds of formula (9) are prepared:

(1R,2S,3R,6S)-[2-ethynyl-3-hydroxybicyclo[4.2.0]octan-7-one;
(1S,2R,3S,6R)-[2-ethynyl-3-hydroxybicyclo[4.2.0]octan-7-one;
(1S,2S,3R,6S)-[2-ethynyl-3-hydroxy-8-endo-methylbicyclo[4.2.0]octan-7-one;
(1R,2R,3S,6R)-[2-ethynyl-3-hydroxy-8-endo-methylbicyclo[4.2.0]octan-7-one;
(1R,2S,3R,6R)-[2-ethynyl-3-hydroxy-6-methoxybicyclo[4.2.0]octan-7-one;
(1S,2R,3S,6S)-[2-ethynyl-3-hydroxy-6-methoxybicyclo[4.2.0]octan-7-one;
(1S,2S,3R,6R)-[2-ethynyl-3-hydroxy-6-methoxy-8-exo-methylbicyclo[4.2.0]octan-7-one;
(1R,2R,3S,6S)-[2-ethynyl-3-hydroxy-6-methoxy-8-exo-methylbicyclo[4.2.0]octan-7-one;
(1S,2S,3R,6R)-[2-ethynyl-3-hydroxy-6-methoxy-8-endo-methylbicyclo[4.2.0]octan-7-one;
(1R,2R,3S,6S)-[2-ethynyl-3-hydroxy-6-methoxy-8-endo-methylbicyclo[4.2.0]octan-7-one;

C. In like manner, following the procedures of paragraph 9.A. above, the following exemplary compounds of formula (9), where Y is hydrogen, or exo or endo-(lower alkyl), are obtained:

(1SR,2RS,3SR,6RS)-2-ethynyl-3-hydroxy-bicyclo[4.2.0]octan-7-one;
(1SR,2RS,3SR,6SR)-2-ethynyl-3-hydroxy-6-methoxybicyclo[4.2.0]octan-7-one;
(1RS,2RS,3SR,6SR)-[2-ethynyl-3-hydroxy-6-methoxy-8-exo-methylbicyclo[4.2.0]octan-7-one;
(1RS,2RS,3SR,6SR)-[2-ethynyl-3-hydroxy-6-methoxy-8-endo-methylbicyclo[4.2.0]octan-7-one;
(1RS,2SR,3RS,6RS)-[2-ethynyl-3-hydroxy-6-ethoxybicyclo[4.2.0]octan-7-one;
(1RS,2SR,3RS,6RS)-[2-ethynyl-3-hydroxy-6-n-butoxybicyclo[4.2.0]octan-7-one;
(1RS,2RS,3SR,6SR)-[2-ethynyl-3-hydroxy-6-ethoxy-8-methylbicyclo[4.2.0]octan-7-one;
(1RS,2RS,3SR,6SR)-2-ethynyl-3-hydroxy-6-methoxy-8-endo-ethylbicyclo[4.2.0]octan-7-one;
(2RS,2RS,3SR,6SR)-2-ethynyl-3-hydroxy-6-methoxy-8-exo-n-butylbicyclo[4.2.0]octan-7-one;
(1RS,2RS,3SR,6SR)-2-ethynyl-3-hydroxy-6-n-butoxy-8-endo-n-butylbicyclo[4.2.0]octan-7-one.

PREPARATION 10

Preparation of
(Z)-(1SR,2SR,3RS,6SR)-4-[2-ethynyl-3-hydroxybicyclo[4.2.0]oct-7-ylidene]butanoic acid and
(E)-(1SR,2SR,3RS,6SR)-4-[2-ethynyl-3-hydroxybicyclo[4.2.0]-oct-7-ylidene]butanoic acid and Related Compounds of Formula (10).

A. A stock solution of dimsyl sodium was prepared by dissolving 1.56 g sodium hydride in 30 ml dimethyl sulfoxide at 65° C. under nitrogen. To a stirred slurry of 2.06 g of 3-carboxypropyltriphenylphosphonium bromide in 10 ml of dimethyl sulfoxide under nitrogen was added 9.4 ml of the stock solution of dimsyl sodium. After 20 min at 23° C. a solution of 160 mg of (1RS,2SR,3RS,6SR)-2-ethynyl-3-hydroxybicyclo[4.2.0]octan-7-one in 1 ml of dimethyl sulfoxide was added in one portion. After 4 hours at 23° C. the mixture was poured on to 15 ml of 5% sodium carbonate solution. This mixture was washed with two 30 ml portions of ethyl acetate and was then acidified with conc. HCl. The aqueous layer was extracted three times with 50 ml portions of diethyl ether. The combined ether extract was concentrated to 20 ml and this was kept at −20° C. for 2 hours. The resulting precipitate was filtered and was discarded. Evaporation of the filtrate gave 200 mg of an oil. This material was purified by silica gel flash chromatography using a solvent mixture of acetic acid-acetone-methylene chloride (0.2:15:85) to give 140 mg of an oil. Further purification by silica gel flash chromatography using a solvent mixture of acetic acid-ethanol-hexane-dichloromethane (0.1:4:62:31) separated the product into the individual (E) and (Z) isomers of the racemic mixture represented by the formula (10), namely (E)-(1SR,2SR,3RS,6SR)-4-[2-ethynyl-3-hydroxybicyclo[4.2.0]oct-7-ylidene]butanoic acid, and (Z)-(1SR,2SR,3RS,6SR)-4-[2-ethynyl-3-hydroxybicyclo[4.2.0]oct-7-ylidene]butanoic acid.

B. In like manner, following the procedure of Preparation 10A above, replacing 3-carboxypropyltriphosphonium bromide with 4-carboxybutyltriphenylphosphonium bromide, the following compounds are prepared:

(E)-(1SR,2SR,3RS,6SR)-4-[2-ethynyl-3-hydroxybicyclo[4.2.0]-oct-7-ylidene]pentanoic acid and (Z)-(1SR,2SR,3RS,6SR)-4-[2-ethynyl-3-hydroxybicyclo[4.2.0]-oct-7-ylidene]pentanoic acid.

C. In like manner, following the procedure of paragraphs 10.A. or 10.B. above, but replacing (1RS,2SR,3RS,6SR)-2-ethynyl-3-hydroxybicyclo[4.2.0]octan-7-one with a single enantiomer of formula (9), prepared as shown in Preparation 9.B., the following exemplary enantiomers of compounds of formula (10) are prepared as the E isomer or the Z isomer:

(1S,2S,3R,6S)-4-[2-ethynyl-3-hydroxybicyclo[4.2.0]oct-7-ylidene]butanoic acid;

(1R,2R,3S,6R)-4-[2-ethynyl-3-hydroxybicyclo[4.2.0]oct-7-ylidene]butanoic acid;

(1S,2S,3R,6S)-5-[2-ethynyl-3-hydroxybicyclo[4.2.0]oct-7-ylidene]pentanoic acid;

(1R,2R,3S,6R)-5-[2-ethynyl-3-hydroxybicyclo[4.2.0]oct-7-ylidene]pentanoic acid;

(1S,2S,3R,6S)-4-[2-ethynyl-3-hydroxy-8-endo-methylbicyclo[4.2.0]oct-7-ylidene]butanoic acid;

(1R,2R,3S,6R)-4-[2-ethynyl-3-hydroxy-8-endo-methylbicyclo[4.2.0]oct-7-ylidene]butanoic acid;

(1R,2S,3R,6R)-4-[2-ethynyl-3-hydroxy-6-methoxybicyclo[4.2.0]oct-7-ylidene]butanoic acid;

(1S,2R,3S,6S)-4-[2-ethynyl-3-hydroxy-6-methoxybicyclo[4.2.0]oct-7-ylidene]butanoic acid;

(1R,2S,3R,6R)-4-[2-ethynyl-3-hydroxy-6-methoxy-8-exo-methylbicyclo[4.2.0]oct-7-ylidene]butanoic acid;

(1S,2R,3S,6S)-4-[2-ethynyl-3-hydroxy-6-methoxy-8-exo-methylbicyclo[4.2.0]oct-7-ylidene]butanoic acid;

(1R,2S,3R,6R)-4-[2-ethynyl-3-hydroxy-6-methoxy-8-endo-methylbicyclo[4.2.0]oct-7-ylidene]butanoic acid;

(1S,2R,3S,6S)-4-[2-ethynyl-3-hydroxy-6-methoxy-8-endo-methylbicyclo[4.2.0]oct-7-ylidene]butanoic acid;

D. In like manner, following the procedure of Preparation 10A or 10B above but replacing the (1RS,2SR,3RS,6SR)-2-ethynyl-3-hydroxybicyclo[4.2.0]octane-7-one with other appropriate racemic mixtures represented by the formulas (9), obtained as described in Preparation 9, the following exemplary racemic mixtures represented by the formula (10) are obtained as the E isomer or the Z isomer:

(1SR,2SR,3RS,6SR)-4-[2-ethynyl-3-hydroxybicyclo[4.2.0]oct-7-ylidene]butanoic acid;

(1SR,2SR,3RS,6SR)-4-[2-ethynyl-3-hydroxy-8-endo-methylbicyclo[4.2.0]oct-7-ylidene]butanoic acid;

(1RS,2SR,3RS,6RS)-4-[2-ethynyl-3-hydroxy-6-methoxybicyclo[4.2.0]oct-7-ylidene]butanoic acid;

(1RS,2SR,3RS,6RS)-4-[2-ethynyl-3-hydroxy-6-methoxy-8-endo-methylbicyclo[4.2.0]oct-7-ylidene]butanoic acid;

(1RS,2SR,3RS,6RS)-4-[2-ethynyl-3-hydroxy-6-methoxy-8-exo-methylbicyclo[4.2.0]oct-7-ylidene]butanoic acid;

(1RS,2SR,3RS,6RS)-5-[2-ethynyl-3-hydroxy-6-methoxy-8-endo-methylbicyclo[4.2.0]oct-7-ylidene]pentanoic acid;

(1RS,2SR,3RS,6RS)-5-[2-ethynyl-3-hydroxy-6-methoxybicyclo[4.2.0]oct-7-ylidene]pentanoic acid;

(1RS,2SR,3RS,6RS)-4-[2-ethynyl-3-hydroxy-6-ethoxybicyclo[4.2.0]oct-7-ylidene]butyric acid;

(1RS,2SR,3RS,6RS)-4-[2-ethynyl-3-hydroxy-6-n-butoxybicyclo[4.2.0]oct-7-ylidene]butyric acid;

(1SR,2SR,3RS,6SR)-4-[2-ethynyl-3-hydroxy-8-exo-ethylbicyclo[4.2.0]oct-7-ylidene]butyric acid;

(1SR,2SR,3RS,6SR)-4-[2-ethynyl-3-hydroxy-8-endo-n-butylbicyclo[4.2.0]oct-7-ylidene]butyric acid;

(1SR,2SR,3RS,6SR)-5-[2-ethynyl-3-hydroxy-8-exo-methylbicyclo[4.2.0]oct-7-ylidene]pentanoic acid;

(1RS,2SR,3RS,6RS)-4-[2-ethynyl-3-hydroxy-6-methoxy-8-exo-ethylbicyclo[4.2.0]oct-7-ylidene]butyric acid;

(1RS,2SR,3RS,6RS)-4-[2-ethynyl-3-hydroxy-6-methoxy-8-endo-n-butylbicyclo[4.2.0]oct-7-ylidene]butyric acid;

(1RS,2SR,3RS,6RS)-4-[2-ethynyl-3-hydroxy-6-n-butoxy-8-exo-n-butylbicyclo[4.2.0]oct-7-ylidene]butyric acid;

(1RS,2SR,3RS,6RS)-5-[2-ethynyl-3-hydroxy-6-methoxy-8-exo-methylbicyclo[4.2.0]oct-7-ylidene]pentanoic acid;

(1RS,2SR,3RS,6RS)-5-[2-ethynyl-3-hydroxy-6-ethoxybicyclo[4.2.0]oct-7-ylidene]pentanoic acid;

(1RS,2SR,3RS,6RS)-5-[2-ethynyl-3-hydroxy-6-n-butoxybicyclo[4.2.0]oct-7-ylidene]pentanoic acid;

PREPARATION 11

Preparation of (Z)-(1S,2S,3R,6S)-4-[2-(3'-oxo-3'-cyclohexylprop-1'-ynyl)-3-hydroxybicyclo[4.2.0]oct-7-ylidene]butanoic acid and Related Compounds of Formula (11)

A. A solution of 60 mg of (Z)-(1S,2S,3R,6S)-4-[2-ethynyl-3-hydroxybicyclo[4.2.0]-oct-7-ylidene]-butanoic acid, prepared as shown in Preparation 10, in 4 ml of tetrahydrofuran under nitrogen is cooled to −60° C. and 0.85 ml of 1.6M n-butyllithium is added. After stirring for 1 hour at −60° C. the reaction mixture is cooled to −78° C. and 90 mg of N-methoxy-N-methylcyclohexanecarboxamide, (prepared by the general procedure described in Tet. Lett., (1981), 3815), is added in 1 ml of tetrahydrofuran. The mixture is allowed to warm to room temperature and is then heated at 65° C. for 1 hour. Aqueous saturated sodium sulfate is added, and the product partitioned between ethyl acetate and aqueous sodium carbonate. The aqueous layer is separated, acidified with dilute hydrochloric acid and extracted with ethyl acetate. The combined extracts are dried over anhydrous sodium sulfate and the solvent removed under reduced pressure. The residue is chromatographed on silica gel, eluting with acetic acid-methanol-methylene chloride(1:6:93), giving (Z)-(1S,2S,3R,6S)-4-[2-(3'-oxo-3'-cyclohexylprop-1'-ynyl)-3-hydroxybicyclo[4.2.0]oct-7-ylidene]butanoic acid.

B. In like manner, following the procedure of Preparation 11.A. above, but replacing the (Z)-(1S,2S,3R,6S)-4-[2-ethynyl-3-hydroxybicyclo[4.2.0]oct-7-ylidene]-butanoic acid with the corresponding E isomer, (E)-(1S,2S,3R,6S)-4-[2-(3'-oxo-3'-cyclohexylprop-1'-ynyl)-3-hydroxybicyclo[4.2.0]oct-7-ylidene]butanoic acid is produced.

C. Similarly, following the procedure of Preparation 11A above and starting with the appropriate E or Z isomer of the optically pure enantiomer represented by the formula (10), prepared as shown in Preparation 10B, in place of (Z)-(1S,2S,3R,6S)-4-[2-ethynyl-3-hydroxybicyclo[4.2.0]oct-7-ylidene]butanoic acid, the corresponding (E) and (Z) isomers of the following exemplary compounds of formula (11) are made:

(1S,2S,3R,6S)-4-[2-(3'-oxo-3'-cyclohexylprop-1'-ynyl)-3-hydroxybicyclo[4.2.0]oct-7-ylidene]butanoic acid;
(1R,2R,3S,6R)-4-[2-(3'-oxo-3'-cyclohexylprop-1'-ynyl)-3-hydroxybicyclo[4.2.0]oct-7-ylidene]butanoic acid;
(1S,2S,3R,6S)-5-[2-(3'-oxo-3'-cyclohexylprop-1'-ynyl)-3-hydroxybicyclo[4.2.0]oct-7-ylidene]pentanoic acid;
(1R,2R,3S,6R)-5-[2-(3'-oxo-3'-cyclohexylprop-1'-ynyl)-3-hydroxybicyclo[4.2.0]oct-7-ylidene]pentanoic acid;
(1S,2S,3R,6S)-4-[2-(3'-oxo-3'-cyclohexylprop-1'-ynyl)-3-hydroxy-8-endo-methyl-bicyclo[4.2.0]oct-7-ylidene]butanoic acid;
(1R,2R,3S,6R)-4-[2-(3'-oxo-3'-cyclohexylprop-1'-ynyl)-3-hydroxy-8-endo-methyl-bicyclo[4.2.0]oct-7-ylidene]butanoic acid;
(1R,2S,3R,6R)-4-[2-(3'-oxo-3'-cyclohexylprop-1'-ynyl)-3-hydroxy-6-methoxybicyclo[4.2.0]oct-7-ylidene]butanoic acid;
(1S,2R,3S,6S)-4-[2-(3'-oxo-3'-cyclohexylprop-1'-ynyl)-3-hydroxy-6-methoxybicyclo[4.2.0]oct-7-ylidene]butanoic acid;
(1R,2S,3R,6R)-4-[2-(3'-oxo-3'-cyclohexylprop-1'-ynyl)-3-hydroxy-6-methoxy-8-exo-methylbicyclo[4.2.0]oct-7-ylidene]butanoic acid;
(1S,2R,3S,6S)-4-[2-(3'-oxo-3'-cyclohexylprop-1'-ynyl)-3-hydroxy-6-methoxy-8-exo-methylbicyclo[4.2.0]oct-7-ylidene]butanoic acid;
(1R,2S,3R,6R)-4-[2-(3'-oxo-3'-cyclohexylprop-1'-ynyl)-3-hydroxy-6-methoxy-8-endo-methylbicyclo[4.2.0]oct-7-ylidene]butanoic acid; and
(1S,2R,3S,6S)-4-[2-(3'-oxo-3'-cyclohexylprop-1'-ynyl)-3-hydroxy-6-methoxy-8-endo-methylbicyclo[4.2.0]oct-7-ylidene]butanoic acid;

D. Similarly, following the procedure of Preparation 11A above and starting with the appropriate E or Z isomer of the racemic mixture represented by the formula (10) in place of (Z)-(1S,2S,3R,6S)-4-[2-ethynyl-3-hydroxybicyclo[4.2.0]-oct-7-ylidene]butanoic acid, obtained as described in Preparation 10, and optionally substituting N-methoxy-N-methylcyclohexanecarboxamide with the appropriate compound of formula $R_3C(O)L$, where L is N-methoxy-N-methylamide, the corresponding (E) and (Z) isomers of the following exemplary racemic mixtures of compounds of formula (11) are made:

(1SR,2SR,3RS,6SR)-4-[2-(3'-oxo-3'-cyclohexylprop-1'-ynyl)-3-hydroxybicyclo[4.2.0]oct-7-ylidene]butanoic acid;
(1SR,2RS,3SR,6SR)-4-[2-(3'-oxo-3'-cyclohexylprop-1'-ynyl)-3-hydroxy-6-methoxybicyclo[4.2.0]oct-7-ylidene]butanoic acid;
(1SR,2RS,3SR,6SR)-4-[2-(3'-oxo-3'-cyclohexylprop-1'-ynyl)-3-hydroxy-6-methoxy-8-exo-methylbicyclo[4.2.0]oct-7-ylidene]butanoic acid;
(1SR,2RS,3SR,6SR)-4-[2-(3'-oxo-3'-cyclohexylprop-1'-ynyl)-3-hydroxy-6-methoxy-8-endo-methylbicyclo[4.2.0]oct-7-ylidene]butanoic acid;
(1SR,2RS,3SR,6SR)-5-[2-(3'-oxo-3'-cyclohexylprop-1'-ynyl)-3-hydroxy-6-methoxybicyclo[4.2.0]oct-7-ylidene]pentanoic acid;
(1SR,2RS,3SR,6SR)-4-[2-(3'-oxo-3'-cyclohexylprop-1'-ynyl)-3-hydroxy-6-ethoxybicyclo[4.2.0]oct-7-ylidene]butyric acid;
(1SR,2RS,3SR,6SR)-4-[2-(3'-oxo-4'-phenoxybut-1'-ynyl)-3-hydroxy-6-methoxybicyclo[4.2.0]oct-7-ylidene]butyric acid;
(1SR,2RS,3SR,6SR)-4-[2-(3'-oxo-4'-(endo-bicyclo[3.1.0]hex-6-yl)but-1'-ynyl)-3-hydroxy-6-methoxybicyclo[4.2.0]oct-7-ylidene]butyric acid;
(1SR,2RS,3SR,6SR)-4-[2-(3'-oxo-4'-(endo-bicyclo[3.1.0]hex-6-yl)but-1'-ynyl)-3-hydroxy-6-methoxy-8-methylbicyclo[4.2.0]oct-7-ylidene]butyric acid;
(1SR,2RS,3SR,6SR)-4-[2-(3'-oxo-4'-phenoxybut-1'-ynyl)3-hydroxy-6-methoxy-8-methylbicyclo[4.2.0]oct-7-ylidene]butyric acid;
(1SR,2RS,3SR,6SR)-4-[2-(3'-oxo-4'-phenoxybut-1'-ynyl)-3-hydroxy-8-methylbicyclo[4.2.0]oct-7-ylidene]butyric acid;
(1SR,2RS,3SR,6SR)-4-[2-(3'-oxo-3'-cyclohexylprop-1'-ynyl)-3-hydroxy-6-n-butoxybicyclo[4.2.0]oct-7-ylidene]butyric acid;
(1RS,2RS,3SR,6RS)-4-[2-(3'-oxo-4'-cyclopentylbut-1'-ynyl)-3-hydroxybicyclo[4.2.0]oct-7-ylidene]butyric acid;
(1SR,2RS,3SR,6SR)-4-[2-(3'-oxo-4'-cyclopentylbut-1'-ynyl)-3-hydroxy-6-methoxybicyclo[4.2.0]oct-7-ylidene]butyric acid;
(1RS,2RS,3SR,6RS)-4-[2-(3'-oxo-4'-cyclohexylbut-1'-ynyl)-3-hydroxybicyclo[4.2.0]oct-7-ylidene]butyric acid;

(1SR,2RS,3SR,6SR)-4-[2-(3'-oxo-4'-cyclohexylbut-1'-ynyl)-3-hydroxy-6-methoxybicyclo[4.2.0]oct-7-ylidene]butyric acid;
(1RS,2RS,3SR,6RS)-4-[2-(3'-oxodec-1'-ynyl)-3-hydroxybicyclo[4.2.0]oct-7-ylidene]butyric acid;
(1SR,2RS,3SR,6SR)-4-[2-(3'-oxodec-1'-ynyl)-3-hydroxy-6-methoxybicyclo[4.2.0]oct-7-ylidene]butyric acid;
(1SR,2RS,3SR,6RS)-4-[2-(3'-oxo-4'-cyclopentylbut-1'-ynyl)-3-hydroxy-6-methoxy-8-exo-methylbicyclo[4.2.0]oct-7-ylidene]butyric acid;
(1SR,2RS,3SR,6SR)-4-[2-(3'-oxo-4'-cyclopentylbut-1'-ynyl)-3-hydroxy-6-methoxy-8-endo-methylbicyclo[4.2.0]oct-7-ylidene]butyric acid;
(1SR,2RS,3SR,6SR)-4-[2-(3'-oxo-3'-cyclohexylprop-1'-ynyl)-3hydroxy-6-methoxy-8-exo-ethylbicyclo[4.2.0]oct-7-ylidene]butyric acid;
(1RS,2RS,3SR,6RS)-4-[2-(3'-oxo-3'-cyclohexylprop-1'-ynyl)-3-hydroxy-8-endo-ethylbicyclo[4.2.0]oct-7-ylidene]butyric acid;
(1SR,2RS,3SR,6SR)-4-[2-(3'-oxo-3'-cyclohexylprop-1'-ynyl)-3-hydroxy-6-methoxy-8-exo-n-butylbicyclo[4.2.0]oct-7-ylidene]butyric acid;
(1SR,2RS,3SR,6SR)-5-[2-(3'-oxo-3'-cyclohexylprop-1'-ynyl)-3-hydroxy-6-ethoxybicyclo[4.2.0]oct-7-ylidene]pentanoic acid; and
(1SR,2RS,3SR,6SR)-5-[2-(3'-oxo-3'-cyclohexylprop-1'-ynyl)-3-hydroxy-6-n-butoxybicyclo[4.2.0]oct-7-ylidene]pentanoic acid.

EXAMPLE 1

Preparation of a mixture of
(Z)-(3'SR,1RS,2RS,3SR,6RS)-4-[2-(3'-hydroxy-3'-cyclohexylprop-1'-ynyl)-3-hydroxybicyclo[4.2.0]oct-7-ylidene]butanoic acid and
(Z)-(3'RS,1RS,2RS,3SR,6RS)-4-[2-(3'-hydroxy-3'-cyclohexylprop-1'-ynyl)-3-hydroxybicyclo[4.2.0]oct-7-ylidene]butanoic acid and Related Compounds of Formula (I)

A. A solution of 60 mg of (Z)-(1SR,2SR,3RS,6SR)-4-[2-ethynyl-3-hydroxybicyclo[4.2.0]-oct-7-ylidene]butanoic acid, prepared as shown in Preparation 10, in 4 ml of tetrahydrofuran under nitrogen was cooled to −60° C. and 0.85 ml of 1.6M n-butyllithium was added. After stirring for 1 hour at −60° C. the reaction mixture was cooled to −78° C. and 0.11 g of cyclohexylcarboxaldehyde added. After 30 minutes aqueous saturated sodium sulfate was added, and the product partitioned between ethyl acetate and aqueous sodium carbonate. The aqueous layer was separated, acidified with dilute hydrochloric acid and extracted with ethyl acetate. The combined extracts were dried over anhydrous sodium sulfate and the solvent removed under reduced pressure. The residue was chromatographed on silica gel, eluting with acetic acid-methanol-methylene chloride (1:6:93), giving 32 mg of a mixture of:
(Z)-(3'SR,1RS,2RS,3SR,6RS)-4-[2-(3'-hydroxy-3'-cyclohexylprop-1'-ynyl)-3-hydroxybicyclo[4.2.0]oct-7-ylidene]butanoic acid and (Z)-(3'RS,1RS,2RS,3SR,6RS)-4-[2-(3'-hydroxy-3'-cyclohexylprop-1'-ynyl)-3-hydroxybicyclo[4.2.0]oct-7-ylidene]butanoic acid.

B. In like manner, following the procedure of Example 1.A. above, but replacing the (Z)-(1SR,2SR,3RS,6SR)-4[2-ethynyl-3-hydroxybicyclo[4.2.0]-oct-7-ylidene]butanoic acid with the corresponding E isomer, a mixture of (E)-(3'SR,1RS,2RS,3SR,6RS)-4-[2-(3'-hydroxy-3'-cyclohexylprop-1'-ynyl)-3-hydroxybicyclo[4.2.0]oct-7-ylidene]butanoic acid and (E)-(3'RS,1RS,2RS,3SR,6RS)-4-[2-(3'-hydroxy-3'-cyclohexyl-prop-1'-ynyl)-3-hydroxybicyclo[4.2.0]oct-7-ylidene]butanoic acid is obtained.

C. Similarly, following the procedure of Example 1A above and starting with the appropriate E or Z isomer of the optically pure enantiomer represented by the formula (10), prepared as shown in Preparation 10B, in place of (Z)-(1SR,2SR,3RS,6SR)-4-[2-ethynyl-3-hydroxybicyclo[4.2.0]oct-7-ylidene]butanoic acid, the corresponding (E) and (Z) isomers of the following exemplary diastereomeric mixtures of formula (Ia) and (Ic) or (Ib) and (Id) are made:
(3'S,1S,2S,3R,6S)- and (3'R,1S,2S,3R,6S)-4-[2-(3'-hydroxy-3'-cyclohexylprop-1'-ynyl)-3-hydroxybicyclo[4.2.0]oct-7-ylidene]butanoic acid;
(3'S,1R,2R,3S,6R)- and (3'R,1R,2R,3S,6R)-4-[2-(3'-hydroxy-3'-cyclohexylprop-1'-ynyl)-3-hydroxybicyclo[4.2.0]oct-7-ylidene]butanoic acid;
(3'S,1S,2S,3R,6S)- and (3'R,1S,2S,3R,6S)-5-[2-(3'-hydroxy-3'-cyclohexylprop-1'-ynyl)-3-hydroxybicyclo[4.2.0]oct-7-ylidene]pentanoic acid;
(3'S,1R,2R,3S,6R)- and (3'R,1R,2R,3S,6R)-5-[2-(3'-hydroxy-3'-cyclohexylprop-1'-ynyl)-3-hydroxybicyclo[4.2.0]oct-7-ylidene]pentanoic acid;
(3'S,1S,2S,3R,6S)- and (3'R,1S,2S,3R,6S)-4-[2-(3'-hydroxy-3'-cyclohexylprop-1'-ynyl)-3-hydroxy-8-endo-methylbicyclo[4.2.0]oct-7-ylidene]butanoic acid;
(3'S,1R,2R,3S,6R)- and (3'R,1R,2R,3S,6R)-4-[2-(3'-hydroxy-3'-cyclohexylprop-1'-ynyl)-3-hydroxy-8-endo-methylbicyclo[4.2.0]oct-7-ylidene]butanoic acid;
(3'S,1R,2S,3R,6R)- and (3'R,1R,2S,3R,6R)-4-[2-(3'-hydroxy-3'-cyclohexylprop-1'-ynyl)-3-hydroxy-6-methoxybicyclo[4.2.0]oct-7-ylidene]butanoic acid;
(3'S,1S,2R,3S,6S)- and (3'R,1S,2R,3S,6S)-4-[2-(3'-hydroxy-3'-cyclohexylprop-1'-ynyl)-3-hydroxy-6-methoxybicyclo[4.2.0]oct-7-ylidene]butanoic acid;
(3'S,1R,2S,3R,6R)- and (3'R,1R,2S,3R,6R)-4-[2-(3'-hydroxy-3'-cyclohexylprop-1'-ynyl)-3-hydroxy-6-methoxy-8-exo-methylbicyclo[4.2.0]oct-7-ylidene]butanoic acid;
(3'S,1S,2R,3S,6S)- and (3'R,1S,2R,3S,6S)-4-[2-(3'-hydroxy-3'-cyclohexylprop-1'-ynyl)-3-hydroxy-6-methoxy-8-exo-methylbicyclo[4.2.0]oct-7-ylidene]butanoic acid;
(3'S,1R,2S,3R,6R)- and (3'R,1R,2S,3R,6R)-4-[2-(3'-hydroxy-3'-cyclohexylprop-1'-ynyl)-3-hydroxy-6-methoxy-8-endo-methylbicyclo[4.2.0]oct-7-ylidene]butanoic acid;
(3'S,1S,2R,3S,6S)- and (3'R,1S,2R,3S,6S)-4-[2-(3'-hydroxy-3'-cyclohexylprop-1'-ynyl)-3-hydroxy-6-methoxy-8-endo-methylbicyclo[4.2.0]oct-7-ylidene]butanoic acid;

D. Similarly, following the procedure of Example 1A above and starting with the appropriate E or Z isomer of the racemic mixture represented by the formula (10) in place of (Z)-(1SR,2SR,3RS,6SR)-4-[2-ethynyl-3-hydroxybicyclo[4.2.0]-oct-7-ylidene]butanoic acid, obtained as described in Preparation 10, and optionally substituting cyclohexylcarboxaldehyde with the appropriate aldehyde or ketone of formula $R_2R_3C=O$, the corresponding (E) and (Z) isomers of the following exemplary mixtures of compounds of formula (I) are made:

(3'SR,1SR,2RS,3SR,6SR)-4-[2-(3'-hydroxy-3'-cyclohexylprop-1'-ynyl)-3-hydroxy-6-methoxybicyclo[4.2.0]oct-7-ylidene]butanoic acid; and (3'RS,1SR,2RS,3SR,6SR)-4-[2-(3'-hydroxy-3'-cyclohexylprop-1'-ynyl)-3-hydroxy-6-methoxybicyclo[4.2.0]oct-7-ylidene]butanoic acid;

(3'SR,1SR,2RS,3SR,6SR)-4-[2-(3'-hydroxy-3'-cyclohexylprop-1'-ynyl)-3-hydroxy-6-methoxy-8-exo-methylbicyclo[4.2.0]oct-7-ylidene]butanoic acid; and (3'RS,1SR,2RS,3SR,6SR)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(3'SR,1SR,2RS,3SR,6SR)-4-[2-(3'-hydroxy-3'-cyclohexylprop-1'-ynyl)-3-hydroxy-6-methoxy-8-endo-methylbicyclo[4.2.0]oct-7-ylidene]butanoic acid; and (3'RS,1SR,2RS,3SR,6SR)-4-[2-(3'-hydroxy-3'-cyclohexylprop-1'-ynyl)-3-hydroxy-6-methoxy-8-endo-methylbicyclo[4.2.0]oct-7-ylidene]butanoic acid;

(3'SR,1SR,2RS,3SR,6SR)-5-[2-(3'-hydroxy-3'-cyclohexylprop-1'-ynyl)-3-hydroxy-6-methoxybicyclo[4.2.0]oct-7-ylidene]pentanoic acid; and (3'RS,1SR,2RS,3SR,6SR)-5-[2-(3'-hydroxy-3'-cyclohexylprop-1'-ynyl)-3-hydroxy-6-methoxybicyclo[4.2.0]oct-7-ylidene]pentanoic acid;

(3'SR,1SR,2RS,3SR,6SR)-4-[2-(3'-hydroxy-3'-cyclohexylprop-1'-ynyl)-3-hydroxy-6-ethoxybicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-ethoxybicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-phenoxybut-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid; and (3'RS,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid; and (3'RS,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-n-butoxybicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-n-butoxybicyclo[4.2.0]oct-7-ylidene]butyric acid;

(3'SR,1RS,2RS,3SR,6RS)-4-[2-(3'-hydroxy-4'-cyclopentylbut-1'-ynyl)-3-hydroxybicyclo[4.2.0]oct-7-ylidene]butyric acid; and (3'RS,1RS,2RS,3SR,6RS)-4-[2-(3'-hydroxy-4'-cyclopentylbut-1'-ynyl)-3-hydroxybicyclo[4.2.0]oct-7-ylidene]butyric acid;

(3'SR,1SR,2RS,3SR,6SR)-4-[2-(3'-hydroxy-4'-cyclopentylbut-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-cyclopentylbut-1'-ynyl)-3-hydroxy-6-methoxybicyclo[4.2.0]oct-7-ylidene]butyric acid;

(3'SR,1RS,2RS,3SR,6RS)-4-[2-(3'-hydroxy-4'-cyclohexylbut-1'-ynyl)-3-hydroxybicyclo[4.2.0]oct-7-ylidene]butyric acid; and (3'RS,1RS,2RS,3SR,6RS)-4-[2-(3'-hydroxy-4'-cyclohexylbut-1'-ynyl)-3-hydroxybicyclo[4.2.0]oct-7-ylidene]butyric acid;

(3'SR,1SR,2RS,3SR,6SR)-4-[2-(3'-hydroxy-4'-cyclohexylbut-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-cyclohexylbut-1'-ynyl)-3-hydroxy-6-methoxybicyclo[4.2.0]oct-7-ylidene]butyric acid;

(3'SR,1RS,2RS,3SR,6RS)-4-[2-(3'-hydroxy-dec-1'-ynyl)-3-hydroxybicyclo[4.2.0]oct-7-ylidene]butyric acid; and (3'RS,1RS,2RS,3SR,6RS)-4-[2-(3'-hydroxy-dec-1'-ynyl)-3-hydroxybicyclo[4.2.0]oct-7-ylidene]butyric acid;

(3'SR,1SR,2RS,3SR,6SR)-4-[2-(3'-hydroxy-dec-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-dec-1'-ynyl)-3-hydroxy-6-methoxybicyclo[4.2.0]oct-7-ylidene]butyric acid;

(3'SR,1SR,2RS,3SR,6RS)-4-[2-(3'-hydroxy-4'-cyclopentylbut-1'-ynyl)-3-hydroxy-6-methoxy-8-exo-methylbicyclo[4.2.0]oct-7-ylidene]butyric acid; and (3'RS,1SR,2RS,3SR,6RS)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'SR,1SR,2RS,3SR,6SR)-4-[2-(3'-hydroxy-4'-cyclopentylbut-1'-ynyl)-3-hydroxy-6-methoxy-8-exo-methylbicyclo[4.2.0]oct-7-ylidene]butyric acid; and (3'RS,1SR,2RS,3SR,6SR)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-methoxy-8-exo-ethylbicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-methoxy-8-exo-ethylbicyclo[4.2.0]oct-7-ylidene]butyric acid;

(3'SR,1RS,2RS,3SR,6RS)-4-[2-(3'-hydroxy-3'-cyclohexylprop-1'-ynyl)-3-hydroxy-8-endo-ethylbicyclo[4.2.0]oct-7-ylidene]butyric acid; and (3'RS,1RS,2RS,3SR,6RS)-4-[2-(3'-hydroxy-3'-hydroxy-3'-cyclohexylprop-1'-ynyl)-3-hydroxy-8-endo-ethylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-methoxy-8-exo-n-butylbicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-methoxy-8-exo-n-butylbicyclo[4.2.0]oct-7-ylidene]butyric acid;

(3'SR,1RS,2RS,3SR,6RS)-4-[2-(3'-hydroxy-3'-cyclohexylprop-1'-ynyl)-3-hydroxy-endo-8-n-butylbicyclo[4.2.0]oct-7-ylidene]butyric acid; and (3'RS,1RS,2RS,3SR,6RS)-4-[2-(3'-hydroxy-3'-cyclohexylprop-1'-ynyl)-3-hydroxy-endo-8-n-butylbicyclo[4.2.0]oct-7-ylidene]butyric acid;

(3'SR,1SR,2RS,3SR,6SR)-5-[2-(3'-hydroxy-3'-cyclohexylprop-1'-ynyl)-3-hydroxy-6-ethoxybicyclo[4.2.0]oct-7-ylidene]pentanoic acid; and (3'RS,1SR,2RS,3SR,6SR)-5-[2-(3'-hydroxy-3'-cyclohexylprop-1'-ynyl)-3-hydroxy-6-ethoxybicyclo[4.2.0]oct-7-ylidene]pentanoic acid;

(3'SR,1SR,2RS,3SR,6SR)-5-[2-(3'-hydroxy-3'-cyclohexylprop-1'-ynyl)-3-hydroxy-6-n-butoxybicyclo[4.2.0]oct-7-ylidene]pentanoic acid; and (3'RS,1SR,2RS,3SR,6SR)-5-[2-(3'-hydroxy-3'-cyclohexylprop-1'-ynyl)-3-hydroxy-6-n-butoxybicyclo[4.2.0]oct-7-ylidene]pentanoic acid.

EXAMPLE 2

Alternative Preparation of a mixture of (Z)-(3'SR,1RS,2RS,3SR,6RS)-4-[2-(3'-hydroxy-3'-cyclohexylprop-1'-ynyl)-3-hydroxy-bicyclo[4.2.0]oct-7-ylidene]butanoic acid and (Z)-(3'RS,1RS,2RS,3SR,6RS)-4-[2-(3'-hydroxy-3'-cyclohexylprop-1'-ynyl)-3-hydroxybicyclo[4.2.0]-oct-7-ylidene]butanoic acid and Related Compounds of Formula (I) where $R_2$ is hydrogen A. A solution of 344 mg of (Z)-(1SR,2SR,3RS,6SR)-4-[2-(3'-oxo-3'-cyclohexylprop-1'-ynyl)-3-hydroxybicyclo[4.2.0]oct-7-ylidene]butanoic acid in 10 ml of methanol is treated at 0° C. with 114 mg of sodium borohydride, and the mixture stirred at 0° C. for 1 hour. The solvent is removed under reduced pressure and the residue partitioned between ethyl acetate and water. The organic layer is dried over magnesium sulfate and the solvent removed under reduced pressure, giving a mixture of (Z)-(3'SR,1RS,2RS,3SR,6RS)-4-[2-(3'-hydroxy-3'-cyclohexylprop-1'-ynyl)-3-hydroxy-bicyclo[4.2.0]oct-7-ylidene]butanoic acid and (Z)-(3'RS,1RS,2RS,3SR,6RS)-4-[2-(3'-hydroxy-3'-cyclohexylprop-1'-ynyl)-3-hydroxybicyclo[4.2.0]-oct-7-ylidene]butanoic acid.

B. In like manner, following the procedure of Example 2.A. above, but replacing the (Z)-(1SR,2SR,3RS,6SR)-4-[2-(3'-oxo-3'-cyclohexylprop-1'-ynyl)-3-hydroxybicyclo[4.2.0]oct-7-ylidene]butanoic acid with the corresponding E isomer, a mixture of (E)-(3'SR,1RS,2RS,3SR,6RS)-4-[2-(3'-hydroxy-3'-cyclohexylprop-1'-ynyl)-3-hydroxybicyclo[4.2.0]oct-7-ylidene]butanoic acid and (E)-(3'RS,1RS,2RS,3SR,6RS)-4-[2-(3'-hydroxy-3'-cyclohexylprop-1'-ynyl)-3-hydroxybicyclo[4.2.0]-oct-7-ylidene]butanoic acid is obtained.

C. Similarly, following the procedure of Example 2A above and starting with the appropriate E or Z isomer of the optically pure enantiomer represented by the formula (11), prepared as shown in Preparation 11B, in place of (Z)-(1SR,2SR,3RS,6SR)-4-[2-(3'-oxo-3'-cyclohexylprop-1'-ynyl)-3-hydroxybicyclo[4.2.0]oct-7-ylidene]butanoic acid, the corresponding (E) and (Z) isomers of the following exemplary diastereomeric mixtures of formula (Ia) and (Ic) or (Ib) and (Id) are made:

(3'S,1S,2S,3R,6S)- and (3'R,1S,2S,3R,6S)-4-[2-(3'-hydroxy-3'-cyclohexylprop-1'-ynyl)-3-hydroxybicyclo[4.2.0]oct-7-ylidene]butanoic acid;

(3'S,1R,2R,3S,6R)- and (3'R,1R,2R,3S,6R)-4-[2-(3'-hydroxy-3'-cyclohexylprop-1'-ynyl)-3-hydroxybicyclo[4.2.0]oct-7-ylidene]butanoic acid;

(3'S,1S,2S,3R,6S)- and (3'R,1S,2S,3R,6S)-5-[2-(3'-hydroxy-3'-cyclohexylprop-1'-ynyl)-3-hydroxybicyclo[4.2.0]oct-7-ylidene]pentanoic acid;

(3'S,1R,2R,3S,6R)- and (3'R,1R,2R,3S,6R)-5-[2-(3'-hydroxy-3'-cyclohexylprop-1'-ynyl)-3-hydroxybicyclo[4.2.0]oct-7-ylidene]pentanoic acid;

(3'S,1S,2S,3R,6S)- and (3'R,1S,2S,3R,6S)-4-[2-(3'-hydroxy-3'-cyclohexylprop-1'-ynyl)-3-hydroxy-8-endo-methylbicyclo[4.2.0]oct-7-ylidene]butanoic acid;

(3'S,1R,2R,3S,6R)- and (3'R,1R,2R,3S,6R)-4-[2-(3'-hydroxy-3'-cyclohexylprop-1'-ynyl)-3-hydroxy-8-endo-methylbicyclo[4.2.0]oct-7-ylidene]butanoic acid;

(3'S,1R,2S,3R,6R)- and (3'R,1R,2S,3R,6R)-4-[2-(3'-hydroxy-3'-cyclohexylprop-1'-ynyl)-3-hydroxy-6-methoxybicyclo[4.2.0]oct-7-ylidene]butanoic acid;

(3'S,1S,2R,3S,6S)- and (3'R,1S,2R,3S,6S)-4-[2-(3'-hydroxy-3'-cyclohexylprop-1'-ynyl)-3-hydroxy-6-methoxybicyclo[4.2.0]oct-7-ylidene]butanoic acid;

(3'S,1R,2S,3R,6R)- and (3'R,1R,2S,3R,6R)-4-[2-(3'-hydroxy-3'-cyclohexylprop-1'-ynyl)-3-hydroxy-6-methoxy-8-exo-methylbicyclo[4.2.0]oct-7-ylidene]-butanoic acid;

(3'S,1S,2R,3S,6S)- and (3'R,1S,2R,3S,6S)-4-[2-(3'-hydroxy-3'-cyclohexylprop-1'-ynyl)-3-hydroxy-6-methoxy-8-exo-methylbicyclo[4.2.0]oct-7-ylidene]-butanoic acid;

(3'S,1R,2S,3R,6R)- and (3'R,1R,2S,3R,6R)-4-[2-(3'-hydroxy-3'-cyclohexylprop-1'-ynyl)-3-hydroxy-6-methoxy-8-endo-methylbicyclo[4.2.0]oct-7-ylidene]-butanoic acid;

(3'S,1S,2R,3S,6S)- and (3'R,1S,2R,3S,6S)-4-[2-(3'-hydroxy-3'-cyclohexylprop-1'-ynyl)-3-hydroxy-6-methoxy-8-endo-methylbicyclo[4.2.0]oct-7-ylidene]-butanoic acid;

D. Similarly, following the procedure of Example 2A above and starting with the appropriate E or Z isomer of the racemic mixture represented by the formula (11) in place of (Z)-(1SR,2SR,3RS,6SR)-4-[2-(3'-oxo-3'-cyclohexylprop-1'-ynyl)-3-hydroxybicyclo[4.2.0]oct-7-ylidene]butanoic acid, obtained as described in Preparation 11, the corresponding (E) and (Z) isomers of the following exemplary mixtures of compounds of formula (I) are made:

(3'SR,1SR,2RS,3SR,6SR)-4-[2-(3'-hydroxy-3'-cyclohexylprop-1'-ynyl)-3-hydroxy-6-methoxybicyclo[4.2.0]oct-7-ylidene]butanoic acid; and (3'RS,1SR,2RS,3SR,6SR)-4-[2-(3'-hydroxy-3'-cyclohexylprop-1'-ynyl)-3-hydroxy-6-methoxybicyclo[4.2.0]oct-7-ylidene]butanoic acid;

(3'SR,1SR,2RS,3SR,6SR)-4-[2-(3'-hydroxy-3'-cyclohexylprop-1'-ynyl)-3-hydroxy-6-methoxy-8-exo-methylbicyclo[4.2.0]oct-7-ylidene]butanoic acid; and (3'RS,1SR,2RS,3SR,6SR)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(3'SR,1SR,2RS,3SR,6SR)-4-[2-(3'-hydroxy-3'-cyclohexylprop-1'-ynyl)-3-hydroxy-6-methoxy-8-endo-methylbicyclo[4.2.0]oct-7-ylidene]butanoic acid; and (3'RS,1SR,2RS,3SR,6SR)-4-[2-(3'-hydroxy-3'-cyclohexylprop-1'-ynyl)-3-hydroxy-6-methoxy-8-endo-methylbicyclo[4.2.0]oct-7-ylidene]butanoic acid;

(3'SR,1SR,2RS,3SR,6SR)-5-[2-(3'-hydroxy-3'-cyclohexylprop-1'-ynyl)-3-hydroxy-6-methoxybicyclo[4.2.0]oct-7-ylidene]pentanoic acid; and (3'RS,1SR,2RS,3SR,6SR)-5-[2-(3'-hydroxy-3'-cyclohexylprop-1'-ynyl)-3-hydroxy-6-methoxybicyclo[4.2.0]oct-7-ylidene]pentanoic acid;

(3'SR,1SR,2RS,3SR,6SR)-4-[2-(3'-hydroxy-3'-cyclohexylprop-1'-ynyl)-3-hydroxy-6-ethoxybicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-ethoxybicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-phenoxybut-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-(endobicyclo[3.1.0]hex-6-yl)but-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid; and (3'RS,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid; and (3'RS,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-n-butoxybicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-n-butoxybicyclo[4.2.0]oct-7-ylidene]butyric acid;

(3'SR,1RS,2RS,3SR,6RS)-4-[2-(3'-hydroxy-4'-cyclopentylbut-1'-ynyl)-3-hydroxybicyclo[4.2.0]oct-7-ylidene]butyric acid; and (3'RS,1RS,2RS,3SR,6RS)-4-[2-(3'-hydroxy-4'-cyclopentylbut-1'-ynyl)-3-hydroxybicyclo[4.2.0]oct-7-ylidene]butyric acid;

(3'SR,1SR,2RS,3SR,6SR)-4-[2-(3'-hydroxy-4'-cyclopentylbut-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-cyclopentylbut-1'-ynyl)-3-hydroxy-6-methoxybicyclo[4.2.0]oct-7-ylidene]butyric acid;

(3'SR,1RS,2RS,3SR,6RS)-4-[2-(3'-hydroxy-4'-cyclohexylbut-1'-ynyl)-3-hydroxybicyclo[4.2.0]oct-7-ylidene]butyric acid; and (3'RS,1RS,2RS,3SR,6RS)-4-[2-(3'-hydroxy-4'-cyclohexylbut-1'-ynyl)-3-hydroxybicyclo[4.2.0]oct-7-ylidene]butyric acid;

(3'SR,1SR,2RS,3SR,6SR)-4-[2-(3'-hydroxy-4'-cyclohexylbut-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-4'-cyclohexylbut-1'-ynyl)-3-hydroxy-6-methoxybicyclo[4.2.0]oct-7-ylidene]butyric acid;

(3'SR,1RS,2RS,3SR,6RS)-4-[2-(3'-hydroxy-dec-1'-ynyl)-3-hydroxybicyclo[4.2.0]oct-7-ylidene]butyric acid; and (3'RS,1RS,2RS,3SR,6RS)-4-[2-(3'-hydroxy-dec-1'-ynyl)-3-hydroxybicyclo[4.2.0]oct-7-ylidene]butyric acid;

(3'SR,1SR,2RS,3SR,6SR)-4-[2-(3'-hydroxy-dec-1'-ynyl)-3-hydroxy-6-methoxybicyclo[4.2.0]oct-7-ylidene]butyric acid; and (3'RS,1SR,2RS,3SR,6SR)-4-[2-(3'-hydroxy-dec-1'-ynyl)-3-hydroxy-6-methoxybicyclo[4.2.0]oct-7-ylidene]butyric acid;

(3'SR,1SR,2RS,3SR,6RS)-4-[2-(3'-hydroxy-4'-cyclopentylbut-1'-ynyl)-3-hydroxy-6-methoxy-8-exo-methylbicyclo[4.2.0]oct-7-ylidene]butyric acid; and (3'RS,1SR,2RS,3SR,6RS)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'SR,1SR,2RS,3SR,6SR)-4-[2-(3'-hydroxy-4'-cyclopentylbut-1'-ynyl)-3-hydroxy-6-methoxy-8-exo-methylbicyclo[4.2.0]oct-7-ylidene]butyric acid; and (3'RS,1SR,2RS,3SR,6SR)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-methoxy-8-exo-ethylbicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-methoxy-8-exo-ethylbicyclo[4.2.0]oct-7-ylidene]butyric acid;

(3'SR,1RS,2RS,3SR,6RS)-4-[2-(3'-hydroxy-3'-cyclohexylprop-1'-ynyl)-3-hydroxy-8-endo-ethylbicyclo[4.2.0]oct-7-ylidene]butyric acid; and (3'RS,1RS,2RS,3SR,6RS)-4-[2-(3'-hydroxy-3'-cyclohexylprop-1'-ynyl)-3-hydroxy-8-endo-ethylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-methoxy-8-exo-n-butylbicyclo[4.2.0]oct-7-ylidene]butyric acid; and (3'RS,1SR,2RS,3SR,6SR)-4-[2-(3'-hydroxy-3'-cyclohexylprop-1'-ynyl)-3-hydroxy-6-methoxy-8-exo-n-butylbicyclo[4.2.0]oct-7-ylidene]butyric acid;

(3'SR,1RS,2RS,3SR,6RS)-4-[2-(3'-hydroxy-3'-cyclohexylprop-1'-ynyl)-3-hydroxy-endo-8-n-butylbicyclo[4.2.0]oct-7-ylidene]butyric acid; and (3'RS,1RS,2RS,3SR,6RS)-4-[2-(3'-hydroxy-3'-cyclohexylprop-1'-ynyl)-3-hydroxy-endo-8-n-butylbicyclo[4.2.0]oct-7-ylidene]butyric acid;

(3'SR,1SR,2RS,3SR,6SR)-5-[2-(3'-hydroxy-3'-cyclohexylprop-1'-ynyl)-3-hydroxy-6-ethoxybicyclo[4.2.0]oct-7-ylidene]pentanoic acid; and (3'RS,1SR,2RS,3SR,6SR)-5-[2-(3'-hydroxy-3'-cyclohexylprop-1'-ynyl)-3-hydroxy-6-ethoxybicyclo[4.2.0]oct-7-ylidene]pentanoic acid;

(3'SR,1SR,2RS,3SR,6SR)-5-[2-(3'-hydroxy-3'-cyclohexylprop-1'-ynyl)-3-hydroxy-6-n-butoxybicyclo[4.2.0]oct-7-ylidene]pentanoic acid; and (3'RS,1SR,2RS,3SR,6SR)-5-[2-(3'-hydroxy-3'-cyclohexylprop-1'-ynyl)-3-hydroxy-6-n-butoxybicyclo[4.2.0]oct-7-ylidene]pentanoic acid.

EXAMPLE 3

Preparation of
(Z)-(3'S,1S,2S,3R,6S)-4-[2-(3'-hydroxy-3'-cyclohexylprop-1'-ynyl)-3-hydroxybicyclo[4.2.0]oct-7-ylidene]butanoic acid and Related Compounds of Formula (I) where R₂ is Hydrogen A. A mixture of 36 mg of (Z)-(1S,2S,3R,6S)-4-[2-(3'-oxo-3'-cyclohexylprop-1'-ynyl)-3-hydroxybicyclo[4.2.0]oct-7-ylidene]butanoic acid and 1.0 ml of a 0.5M solution of β-isopinocampheyl-9-borabicyclo[3.3.1]nonane in tetrahydrofuran (Aldrich "S-Alpine-Borane") is evaporated to dryness and the resulting residue heated under nitrogen at 80° C. for 18 hours. The mixture is cooled to room temperature and excess reagent destroyed by the addition of 0.03 ml of propionaldehyde. The residue is then diluted with 2 ml of tetrahydrofuran, followed by 0.2 ml of 3N sodium hydroxide. A solution of 30% sodium peroxide (0.2 ml) is added dropwise and the mixture heated at 40° C. for 3 hours. The mixture is then cooled, partitioned between ether and water and extracted thoroughly with ether. The aqueous phase is then acidified with dilute hydrochloric acid and extracted with ethyl acetate. The extract is dried over magnesium sulfate, the solvent removed under reduced pressure and the residue chromatographed on silica gel, eluting with acetic acid-methanol-methylene chloride (1:6:93) to give (Z)-(3'S,1S,2S,3R,6S)-4-[2-(3'-hydroxy-3'-cyclohexylprop-1'-ynyl)-3-hydroxybicyclo[4.2.0]oct-7-ylidene]butanoic acid.

B. In like manner, following the procedure of Example 3.A. above, but replacing the (Z)-(1S,2S,3R,6S)-4-[2-(3'-oxo-3'-cyclohexylprop-1'-ynyl)-3-hydroxybicyclo[4.2.0]oct-7-ylidene]butanoic acid with the corresponding E isomer, (E)-(3'S,1S,2S,3R,6S)-4-[2-(3'-hydroxy-3'-cyclohexylprop-1'-ynyl)-3-hydroxybicyclo[4.2.0]oct-7-ylidene]butanoic acid is obtained.

C. Similarly, following the procedure of Example 3A above and starting with the appropriate (E) or (Z) isomer of the optically pure enantiomer represented by the formula (11), prepared as shown in Preparation 11B, in place of (Z)-(1S,2S,3R,6S)-4-[2-(3'-oxo-3'-cyclohexylprop-1'-ynyl)-3-hydroxybicyclo[4.2.0]oct-7-ylidene]butanoic acid, the corresponding (E) and (Z) isomers of the following exemplary compounds of formula (Ia) and (Id) are made:

(3'S,1S,2S,3R,6S)-4-[2-(3'-hydroxy-3'-cyclohexylprop-1'-ynyl)-3-hydroxybicyclo[4.2.0]oct-7-ylidene]butanoic acid;

(3'S,1R,2R,3S,6R)-4-[2-(3'-hydroxy-3'-cyclohexylprop-1'-ynyl)-3-hydroxybicyclo[4.2.0]oct-7-ylidene]butanoic acid;

(3'S,1S,2S,3R,6S)-5-[2-(3'-hydroxy-3'-cyclohexylprop-1'-ynyl)-3-hydroxybicyclo[4.2.0]oct-7-ylidene]pentanoic acid;

(3'S,1R,2R,3S,6R)-5-[2-(3'-hydroxy-3'-cyclohexylprop-1'-ynyl)-3-hydroxybicyclo[4.2.0]oct-7-ylidene]pentanoic acid;

(3'S,1S,2S,3R,6S)-4-[2-(3'-hydroxy-3'-cyclohexylprop-1'-ynyl)-3-hydroxy-8-endo-methyl-bicyclo[4.2.0]oct-7-ylidene]butanoic acid;

(3'S,1R,2R,3S,6R)-4-[2-(3'-hydroxy-3'-cyclohexylprop-1'-ynyl)-3-hydroxy-8-endo-methyl-bicyclo[4.2.0]oct-7-ylidene]butanoic acid;

(3'S,1R,2S,3R,6R)-4-[2-(3'-hydroxy-3'-cyclohexylprop-1'-ynyl)-3-hydroxy-6-methoxybicyclo[4.2.0]oct-7-ylidene]butanoic acid;

(3'S,1S,2R,3S,6S)-4-[2-(3'-hydroxy-3'-cyclohexyprop-1'-ynyl) -3-hydroxy-6-methoxybicyclo[4.2.0]oct-7-ylidene]butanoic acid;

(3'S,1R,2S,3R,6R)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(3'S,1S,2R,3S,6S)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(3'S,1R,2S,3R,6R)-4-[2-(3'-hydroxy-3'-cyclohexylprop-1'-ynyl)-3-hydroxy-6-methoxy-8-endo-methylbicyclo[4.2.0]oct-7-ylidene]butanoic acid;

(3'S,1S,2R,3S,6S)-4-[2-(3'-hydroxy-3'-cyclohexylprop-1'-ynyl)-3-hydroxy-6-methoxy-8-endo-methylbicyclo[4.2.0]oct-7-ylidene]butanoic acid;

D. Similarly, following the procedure of Example 3A above and starting with the appropriate E or Z isomer of the racemic mixture represented by the formula (11) in place of (Z)-(1S,2S,3R,6S)-4-[2-(3'-oxo-3'-cyclohexylprop-1'-ynyl)-3-hydroxybicyclo[4.2.0]oct-7-ylidene]butanoic acid, obtained as described in Preparation 11, the corresponding (E) and (Z) isomers of the following exemplary compounds of formula (I) are made:

(3'SR,1SR,2RS,3SR,6SR)-4-[2-(3'-hydroxy-3'-cyclohexylprop-1'-ynyl)-3-hydroxy-6-methoxybicyclo[4.2.0]oct-7-ylidene]butanoic acid;

(3'SR,1SR,2RS,3SR,6SR)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(3'SR,1SR,2RS,3SR,6SR)-4-[2-(3'-hydroxy-3'-cyclohexylprop-1'-ynyl)-3-hydroxy-6-methoxy-8-endo-methylbicyclo[4.2.0]oct-7-ylidene]butanoic acid;

(3'SR,1SR,2RS,3SR,6SR)-5-[2-(3'-hydroxy-3'-cyclohexylprop-1'-ynyl)-3-hydroxy-6-methoxybicyclo[4.2.0]oct-7-ylidene]pentanoic acid;

(3'SR,1SR,2RS,3SR,6SR)-4-[2-(3'-hydroxy-3'-cyclohexylprop-1'-ynyl)-3-hydroxy-6-ethoxybicyclo[4.2.0]oct-7-yldiene]butyric acid;

(3'SR,1SR,2RS,3SR,6SR)-4-[2-(3'-hydroxy-4'-phenoxybut-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-(endo-bicyclo[3.1.0]hex-6-yl)but-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-(endo-bicyclo[3.1.0]hex-6-yl)but-1'-ynyl)-3-hydroxy-6-methoxybicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid;

(3'SR,1SR,2RS,3SR,6SR)-4-[2-(3'-hydroxy-4'-phenoxybut-1'-ynyl)-3-hydroxy-6-methoxy-8-methylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-n-butoxybicyclo[4.2.0]oct-7-ylidene]butyric acid;

(3'SR,1RS,2RS,3SR,6RS)-4-[2-(3'-hydroxy-4'-cyclopentylbut-1'-ynyl)-3-hydroxybicyclo[4.2.0]oct-7-ylidene]butyric acid;

(3'SR,1SR,2RS,3SR,6SR)-4-[2-(3'-hydroxy-4'-cyclopentylbut-1'-ynyl)-3-hydroxy-6-methoxybicyclo-[4.2.0]oct-7-ylidene]butyric acid;

(3'SR,1RS,2RS,3SR,6RS)-4-[2-(3'-hydroxy-4'-cyclohexylbut-1'-ynyl)-3-hydroxybicyclo[4.2.0]oct-7-ylidene]butyric acid;

(3'SR,1SR,2RS,3SR,6SR)-4-[2-(3'-hydroxy-4'-cyclohexylbut-1'-ynyl)-3-hydroxy-6-methoxybicyclo[4.2.0]oct-7-ylidene]butyric acid;

(3'SR,1RS,2RS,3SR,6RS)-4-[2-(3'-hydroxy-dec-1'-ynyl)-3-hydroxybicyclo[4.2.0]oct-7-ylidene]butyric acid;

(3'SR,1SR,2RS,3SR,6SR)-4-[2-(3'-hydroxy-dec-1'-ynyl)-3-hydroxy-6-methoxybicyclo[4.2.0]oct-7-ylidene]butyric acid;

(3'SR,1RS,2RS,3SR,6RS)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'SR,1SR,2RS,3SR,6SR)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-methoxy-8-exo-ethylbicyclo[4.2.0]oct-7-ylidene]butyric acid;

(3'SR,1RS,2RS,3SR,6RS)-4-[2-(3'-hydroxy-3'-cyclohexylprop-1'-ynyl)-3-hydroxy-8-endo-ethylbicyclo[4.2.0]oct-7-ylidene]butyric acid;

(3'SR,1SR,2RS,3SR,6SR)-4-[2-(3'-hydroxy-3'-cyclohexylprop-1'-ynyl)-3-hydroxy-6-methoxy-8-exo-n-butylbicyclo[4.2.0]oct-7-ylidene]butyric acid;

(3'SR,1RS,2RS,3SR,6RS)-4-[2-(3'-hydroxy-3'-cyclohexylprop-1'-ynyl)-3-hydroxy-endo-8-n-butylbicyclo[4.2.0]oct-7-ylidene]butyric acid;

(3'SR,1SR,2RS,3SR,6SR)-5-[2-(3'-hydroxy-3'-cyclohexylprop-1'-ynyl)-3-hydroxy-6-ethoxybicyclo[4.2.0]oct-7-ylidene]pentanoic acid; and (3'SR,1SR,2RS,3SR,6SR)-5-[2-(3'-hydroxy-3'-cyclohexylprop-1'-ynyl)-3-hydroxy-6-n-butoxybicyclo[4.2.0]oct-7-ylidene]pentanoic acid;

EXAMPLE 4

Separation of
(Z)-(3'S,1S,2S,3R,6S)-4-[2-(3'-hydroxy-3'-cyclohexyl-prop-1'-ynyl)-3-hydroxybicyclo[4.2.0]oct-7-ylidene]-butanoic acid and
(Z)-(3'R,1S,2S,3R,6S)-4-[2-(3'-hydroxy-3'-cyclohexyl-prop-1'-ynyl)-3-hydroxybicyclo[4.2.0]oct-7-ylidene]-butanoic acid and Related Compounds of Formula (Ia) and (Ic) or (Ib) and (Id)

To 500 mg of the diastereoisomeric mixture (Z)-(3'S,1S,2S,3R,6S)- and (Z)-(3'R,1S,2S,3R,6S)-4-[2-(3'-hydroxy-3'-cyclohexyl-prop-1'-ynyl)-3-hydroxybicyclo[4.2.0]oct-7-ylidene]butanoic acid obtained as described in Example 1, in 15 ml of diethyl ether is added 500 mg of dicobalt octacarbonyl. The mixture is stirred for 30 minutes at 20° C. The mixture is diluted with 20 ml of diethyl ether and filtered. Solvent is removed from the filtrate under reduced pressure and the residue chromatographed on silica gel, eluting with acetic acid:diethyl ether:methylene chloride (0.25:15:85) to give two separate components A and B. Component A, the first eluted compound, is dissolved in 20 ml of acetone/water (9:1) and 1.2 g of ceric ammonium nitrate is added in small portions until an orange color persists. The solution is then diluted with 50 ml of water and extracted with ethyl acetate. The ethyl acetate is removed under reduced pressure and the residue chromatographed on silica gel, eluting with acetic acid:methanol:methylene chloride (0.25:5:95), to give (3'S,1S,2S,3R,6S)-4-[2-(3'-hydroxy-3'-cyclohexylprop-1'-ynyl)-3-hydroxybicyclo[4.2.0]oct-7-ylidene]butanoic acid. Similarly component B is converted to (3'R,1S,2S,3R,6S)-4-[2-(3'-hydroxy-3'-cyclohexylprop-1'-ynyl)-3-hydroxybicyclo[4.2.0]oct-7-ylidene]butanoic acid.

B. In like manner, following the procedure of Example 4.A. above, but replacing the mixture of (Z)-(3'S,1S,2S,3R,6S)- and (Z)-(3'R,1S,2S,3R,6S)-4-[2-(3'-hydroxy-3'-cyclohexyl-prop-1'-ynyl)-3-hydroxybicyclo[4.2.0]oct-7-ylidene]butanoic acid with the corresponding mixture of (E) isomers, (E)-(3'S,1S,2S,3R,6S)-4-[2-(3'-hydroxy-3'-cyclohexylprop-1'-ynyl)-3-hydroxybicyclo[4.2.0]oct-7-ylidene]butanoic acid and (E)-(3'R,1S,2S,3R,6S)-4-[2-(3'-hydroxy-3'-cyclohexylprop-1'-ynyl)-3-hydroxybicyclo[4.2.0]oct-7-ylidene]butanoic acid and is obtained.

C. Similarly, following the procedure of Example 4A above and starting with the appropriate (E) or (Z) isomer of the diastereoisomeric mixture represented by the formula (Ia) and (Ic) or (Ib) and (Id), prepared as shown in Example 1, in place of the mixture of (Z)-(3'S,1S,2S,3R,6S)- and (Z)-(3'R,2S,3R,6S)-4-[2-(3'-hydroxy-3'-cyclohexyl-prop-1'-ynyl)-3-hydroxybicyclo[4.2.0]oct-7-ylidene]butanoic acid, the corresponding (E) and (Z) isomers of the following exemplary individual compounds of formula (I) are separated:

(3'S,1R,2R,3S,6R)- and (3'R,1R,2R,3S,6R)-4-[2-(3'-hydroxy-3'-cyclohexylprop-1'-ynyl)-3-hydroxybicyclo[4.2.0]oct-7-ylidene]butanoic acid;

(3'S,1S,2S,3R,6S)- and (3'R,1S,2S,3R,6S)-5-[2-(3'-hydroxy-3'-cyclohexylprop-1'-ynyl)-3-hydroxybicyclo[4.2.0]oct-7-ylidene]pentanoic acid;

(3'S,1R,2R,3S,6R)- and (3'R,1R,2R,3S,6R)-5-[2-(3'-hydroxy-3'-cyclohexylprop-1'-ynyl)-3-hydroxybicyclo[4.2.0]oct-7-ylidene]pentanoic acid;

(3'S,1S,2S,3R,6S)- and (3'R,1S,2S,3R,6S)-4-[2-(3'-hydroxy-3'-cyclohexylprop-1'-ynyl)-3-hydroxy-8-endo-methylbicyclo[4.2.0]oct-7-ylidene]butanoic acid;

(3'S,1R,2R,3S,6R)- and (3'R,1R,2R,3S,6R)-4-[2-(3'-hydroxy-3'-cyclohexylprop-1'-ynyl)-3-hydroxy-8-endo-methylbicyclo[4.2.0]oct-7-ylidene]butanoic acid;

(3'S,1R,2S,3R,6R)- and (3'R,1R,2S,3R,6R)-4-[2-(3'-hydroxy-3'-cyclohexylprop-1'-ynyl)-3-hydroxy-6-methoxybicyclo[4.2.0]oct-7-ylidene]butanoic acid;

(3'S,1S,2R,3S,6S)- and (3'R,1S,2R,3S,6S)-4-[2-(3'-hydroxy-3'-cyclohexylprop-1'-ynyl)-3-hydroxy-6-methoxybicyclo[4.2.0]oct-7-ylidene]butanoic acid;

(3'S,1R,2S,3R,6R)- and (3'R,1R,2S,3R,6R)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(3'S,1S,2R,3S,6S)- and (3'R,1S,2R,3S,6S)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(3'S,1R,2S,3R,6R)- and (3'R,1R,2S,3R,6R)-4-[2-(3'-hydroxy-3'-cyclohexylprop-1'-ynyl)-3-hydroxy-6-methoxy-8-endo-methylbicyclo[4.2.0]oct-7-ylidene]butanoic acid;

(3'S,1S,2R,3S,6S)- and (3'R,1S,2R,3S,6S)-4-[2-(3'-hydroxy-3'-cyclohexylprop-1'-ynyl)-3-hydroxy-6-methoxy-8-endo-methylbicyclo[4.2.0]oct-7-ylidene]butanoic acid.

What we claim is:

1. A compound, as a single stereoisomer or a mixture of stereoisomers, represented by the formula (10):

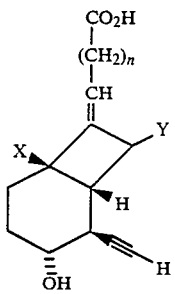

(10)

wherein:
X is hydrogen or lower alkoxy;
Y is hydrogen, exo-(lower alkyl) or endo-(lower alkyl); and
n is an integer of 2-4.

2. The compound of claim 1, wherein X is hydrogen or methoxy and Y is hydrogen or methyl.

3. The compound of claim 2, which is the Z isomer.

4. The compound of claim 3, wherein n is 2 and X and Y are hydrogen, namely (Z)-(1S,2S,3R,6S)-4-[2-ethynyl-3-hydroxybicyclo[4.2.0]-oct-7-ylidene]butanoic acid.

5. The racemic modification of the compound of claim 4, namely (Z)-(1SR,2SR,3RS,6SR)-4-[2-ethynyl-3-hydroxybicyclo[4.2.0]-oct-7-ylidene]butanoic acid.

6. The compound of claim 3, wherein n is 2, X is methoxy and Y is hydrogen, namely (1S,2R,3S,6S)-4-[2-ethynyl-3-hydroxy-6-methoxybicyclo[4.2.0]oct-7-ylidene]butanoic acid.

7. The racemic modification of the compound of claim 6, namely (1RS,2SR,3RS,6RS)-4-[2-ethynyl-3-hydroxy-6-methoxybicyclo[4.2.0]oct-7-ylidene]-butanoic acid.

8. The compound of claim 3, wherein n is 2, X is hydrogen and Y is endo-methyl, namely (1S,2S,3R,6S)-4-[2-ethynyl-3-hydroxy-8-endo-methylbicyclo[4.2.0]oct-7-ylidene]butanoic acid.

9. The racemic modification of the compound of claim 8, namely (1SR,2SR,3RS,6SR)-4-[2-ethynyl-3-hydroxy-8-endo-methylbicyclo[4.2.0]oct-7-ylidene]-butanoic acid.

10. The compound of claim 3, wherein n is 2, X is methoxy and Y is endo-methyl, namely (1S,2R,3S,6S)-4-[2-ethynyl-3-hydroxy-6-methoxy-8-endo-methylbicyclo[4.2.0]-oct-7-ylidene]butanoic acid.

11. The racemic modification of the compound of claim 10, namely (1RS,2SR,3RS,6RS)-4-[2-ethynyl-3-hydroxy-6-methoxy-8-endo-methylbicyclo[4.2.0]oct-7-ylidene]butanoic acid.

* * * * *